(12) United States Patent  
Fang

(10) Patent No.: US 11,529,084 B2  
(45) Date of Patent: Dec. 20, 2022

(54) CARDIOVASCULAR DETECTION SYSTEM AND METHOD

(71) Applicant: Dan Qun Fang, Temple City, CA (US)

(72) Inventor: Dan Qun Fang, Temple City, CA (US)

( * ) Notice: Subject to any disclaimer, the term of this patent is extended or adjusted under 35 U.S.C. 154(b) by 367 days.

(21) Appl. No.: 14/848,266

(22) Filed: Sep. 8, 2015

(65) Prior Publication Data

US 2017/0065194 A1 Mar. 9, 2017

(51) Int. Cl.
| | |
|---|---|
| A61B 5/318 | (2021.01) |
| A61B 5/00 | (2006.01) |
| A61B 5/30 | (2021.01) |
| A61B 5/316 | (2021.01) |
| A61B 5/349 | (2021.01) |
| A61B 5/0245 | (2006.01) |
| A61B 5/361 | (2021.01) |

(52) U.S. Cl.
CPC .............. *A61B 5/318* (2021.01); *A61B 5/30* (2021.01); *A61B 5/316* (2021.01); *A61B 5/349* (2021.01); *A61B 5/7235* (2013.01); *A61B 5/0245* (2013.01); *A61B 5/361* (2021.01); *A61B 5/7257* (2013.01)

(58) Field of Classification Search
CPC ..... A61B 5/0402; A61B 5/0452; A61B 5/046; A61B 5/04012

USPC .......................................................... 600/509
See application file for complete search history.

(56) References Cited

U.S. PATENT DOCUMENTS

| | | | | |
|---|---|---|---|---|
| 2002/0058612 | A1* | 5/2002 | Franco | A61K 38/1825 514/8.1 |
| 2005/0240112 | A1* | 10/2005 | Fang | A61B 5/0452 600/509 |
| 2007/0191895 | A1* | 8/2007 | Foreman | A61N 1/36114 607/14 |
| 2008/0015439 | A1* | 1/2008 | Raju | A61B 8/488 600/455 |
| 2009/0234202 | A1* | 9/2009 | Goix | A61B 5/412 600/301 |
| 2011/0263995 | A1* | 10/2011 | Chen | A61B 5/0452 600/515 |

\* cited by examiner

*Primary Examiner* — Catherine M Voorhees  
*Assistant Examiner* — Roland Dinga  
(74) *Attorney, Agent, or Firm* — WPAT Law, P.C.; Anthony King

(57) ABSTRACT

The detection and diagnosis of a variety of cardiovascular disorders and levels of heart condition, using a novel method and system, according to a comprehensive analysis of cardiac electrical signal via the frequency domain, time domain, spatial domain.

3 Claims, 20 Drawing Sheets

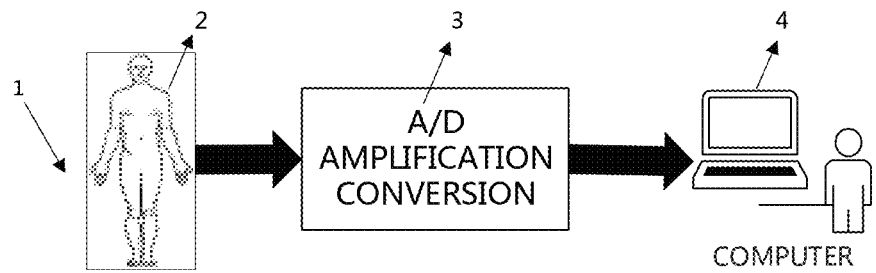
Fig.1 Block diagram
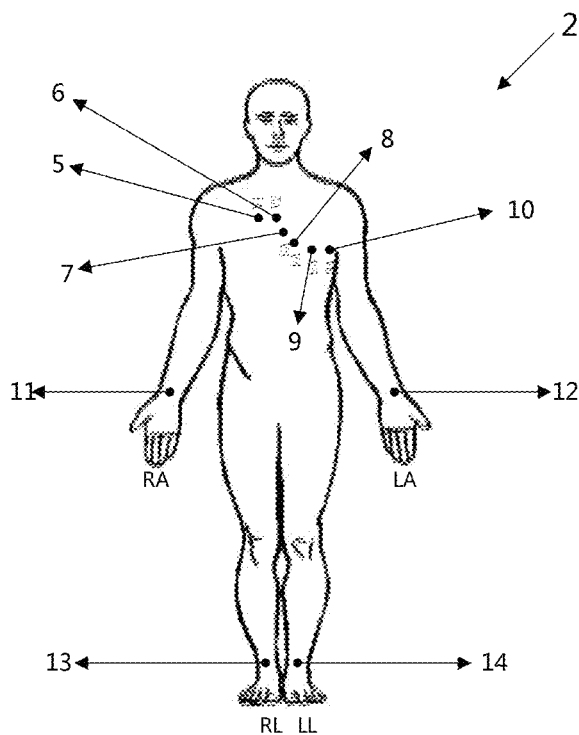
Fig.2 The lead to position on the body
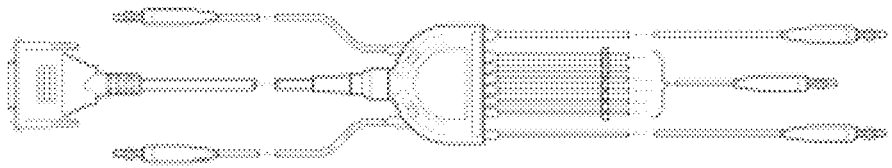
Fig.3 The 12 led ECG Cable

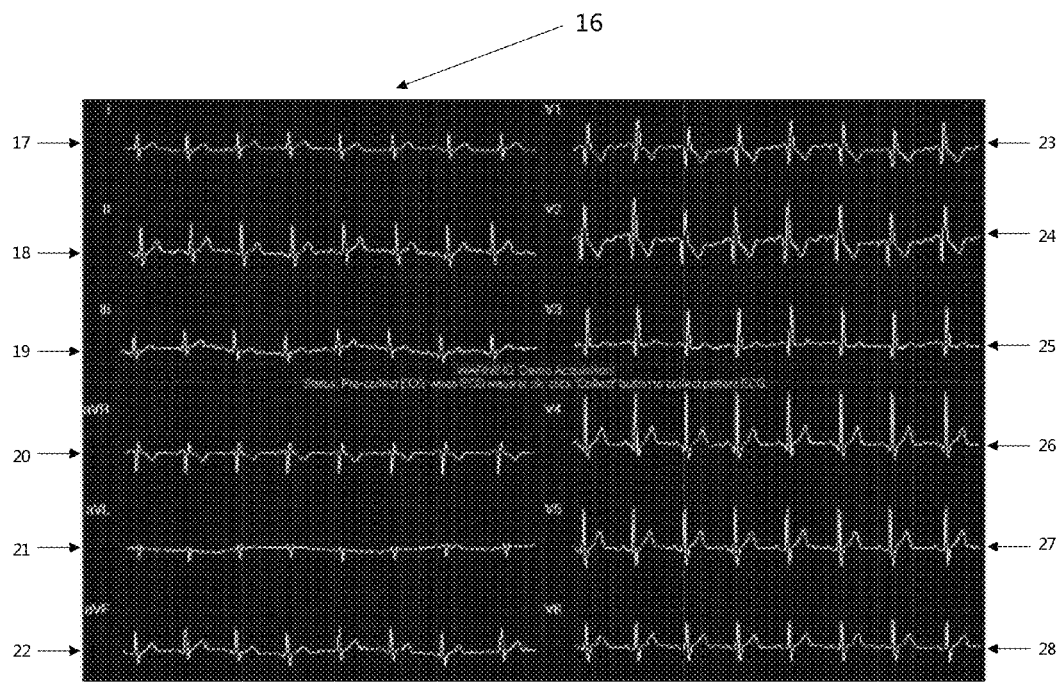
Fig.4 The 12 lead ECG
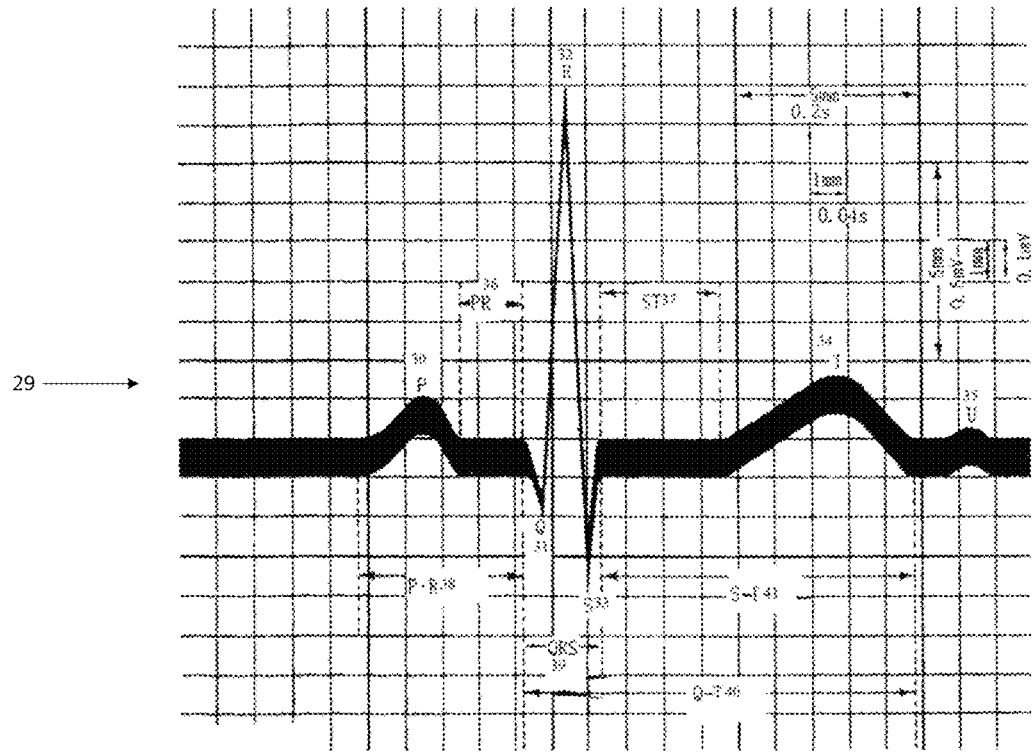
Fig.5 The wave, segment, interval of ECG Fig.6 Normal quantum power spectrum

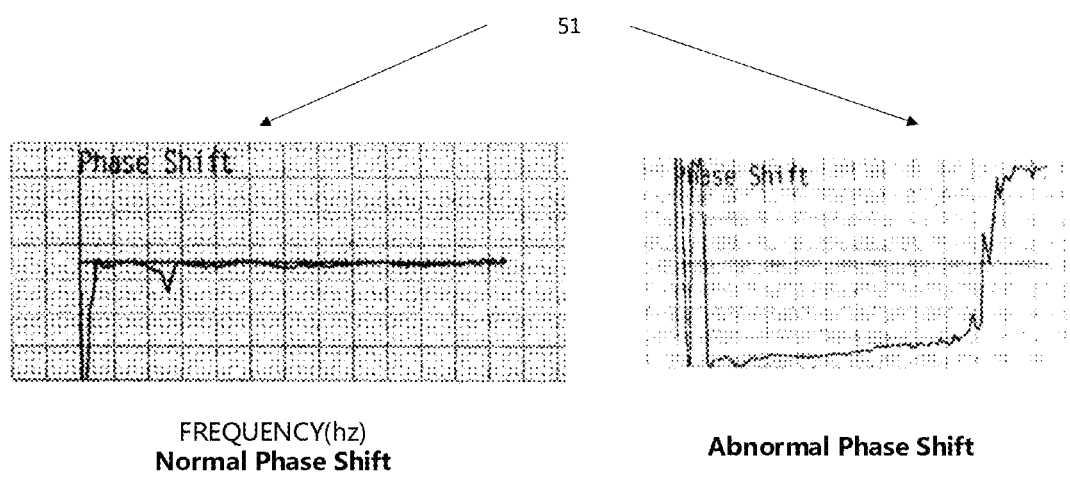
Fig.7A Phase Shift

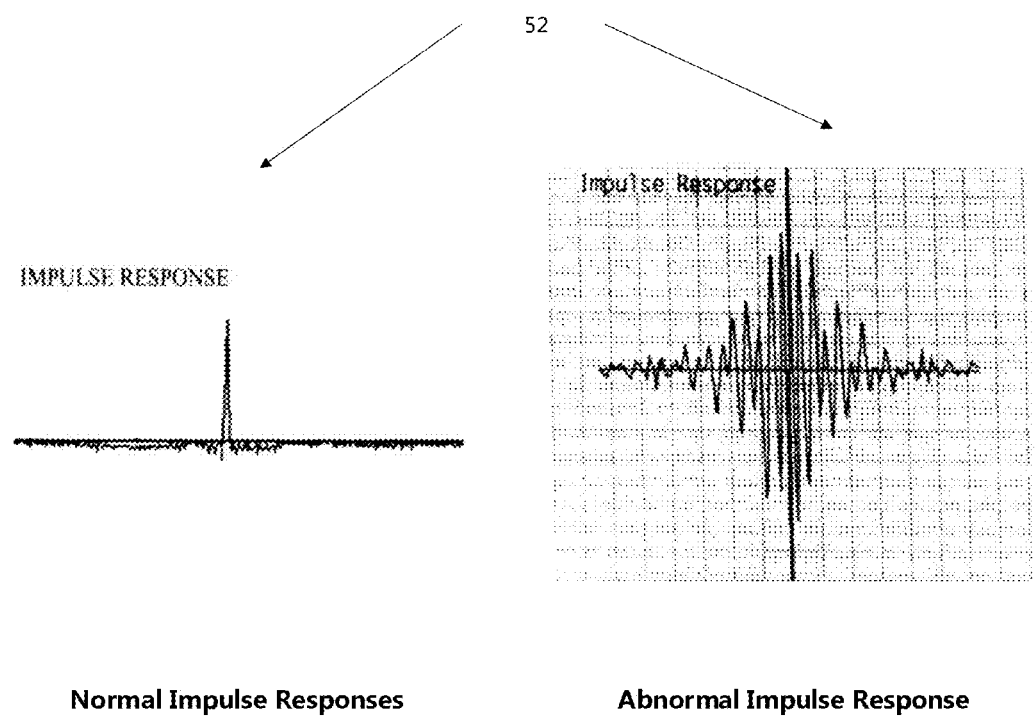
Fig.7B Impulse Response

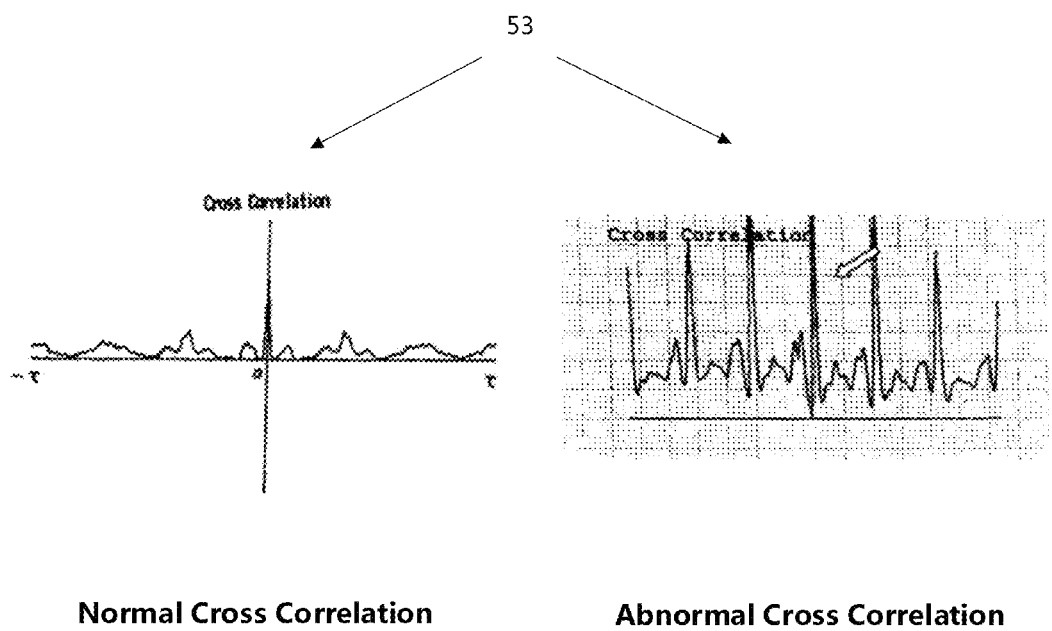
Fig.7C Cross - Correlation

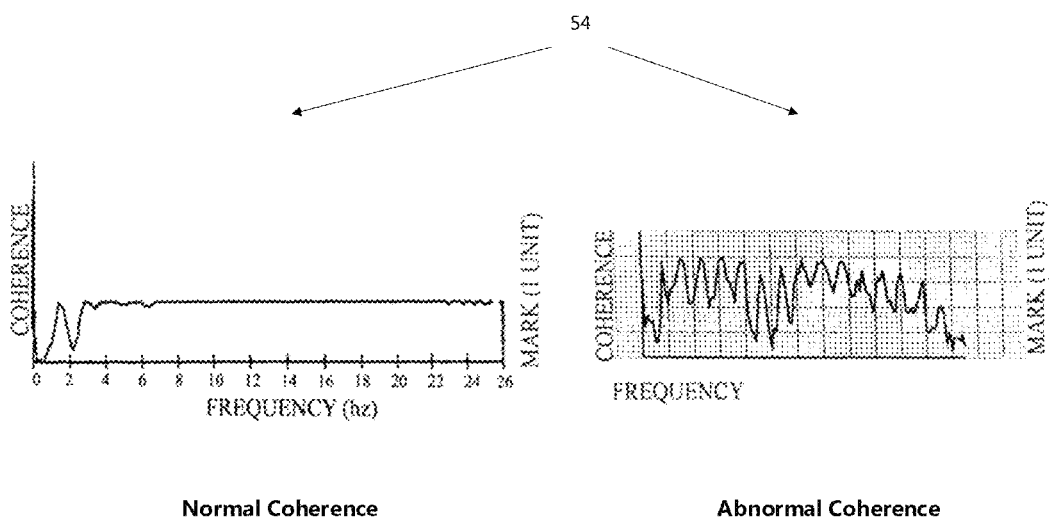
Fig.7D Coherence

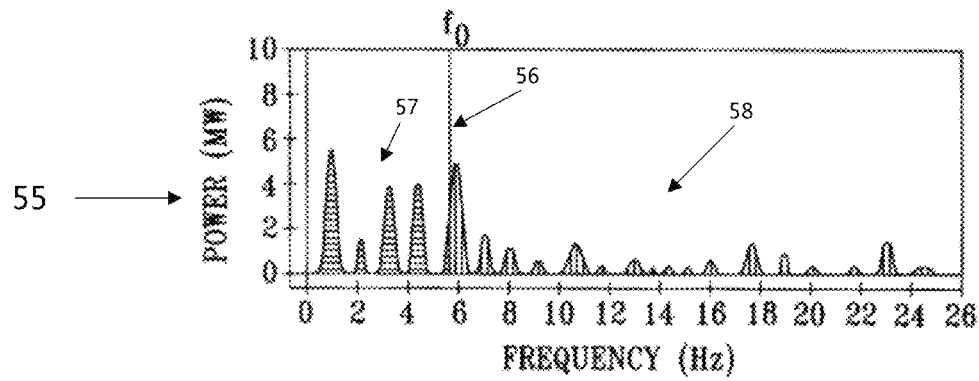
Fig.8 Basing of the value
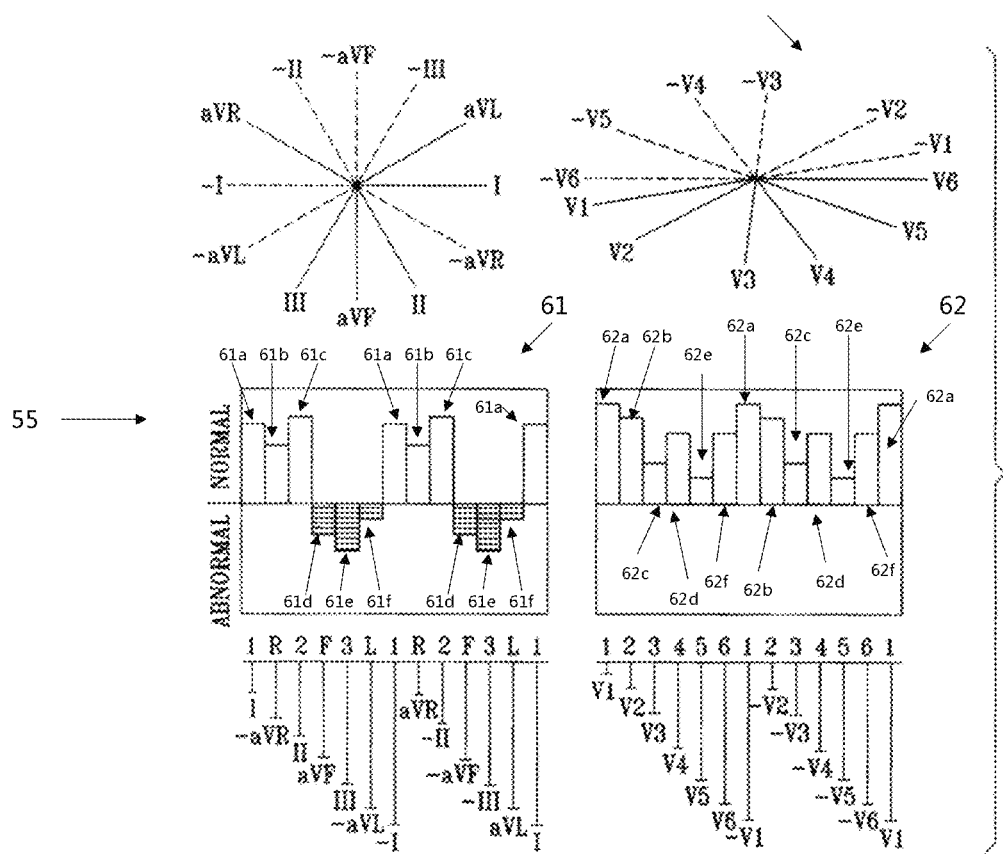
Fig.9 Location map of the evaluation standard

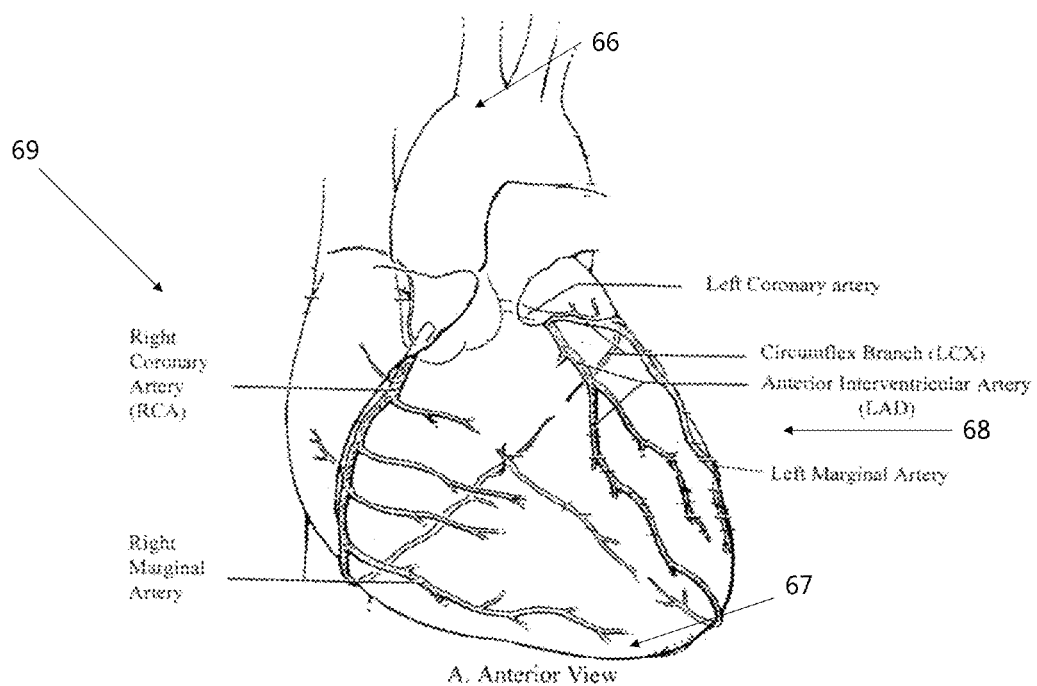
Fig.11A LAD and its branch and RCA and its branch
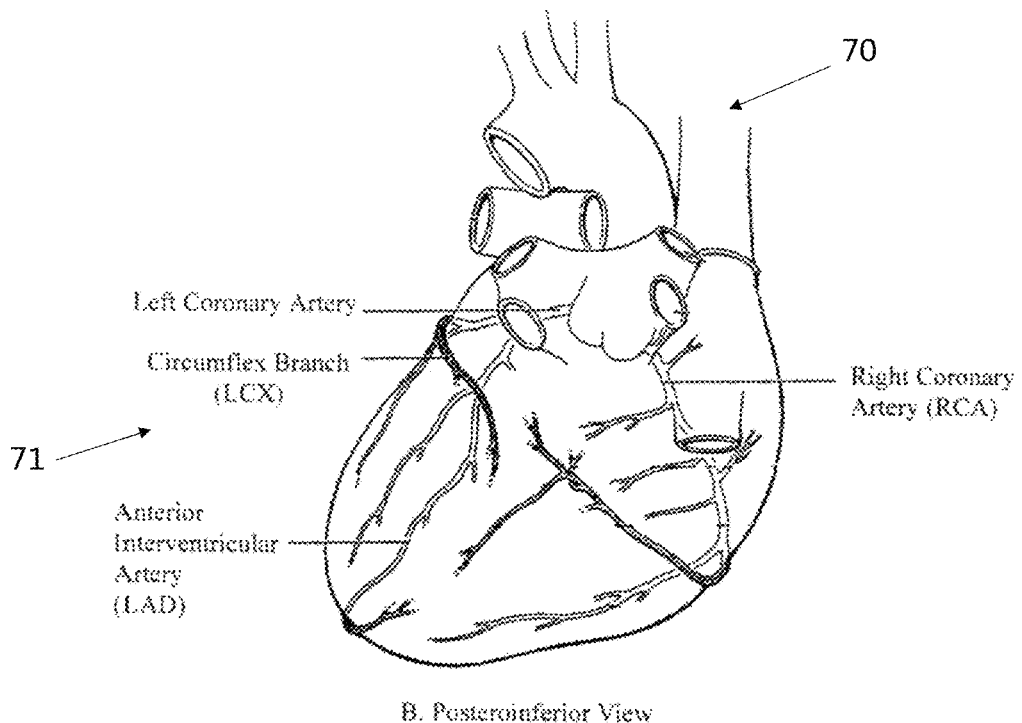
Fig.11B LCX and its branch

Fig.12 Heart Level

Fig. 13 (continued)
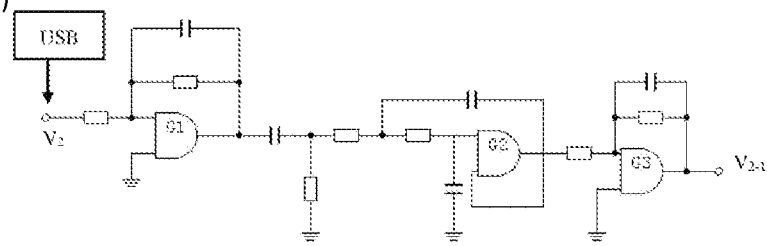
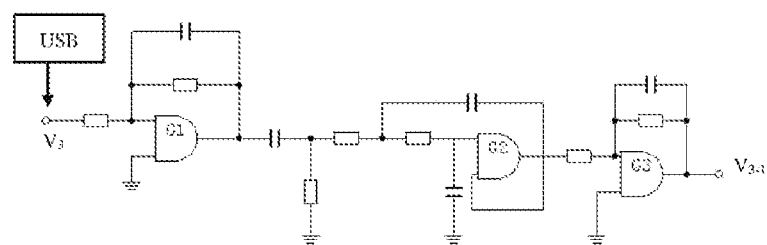
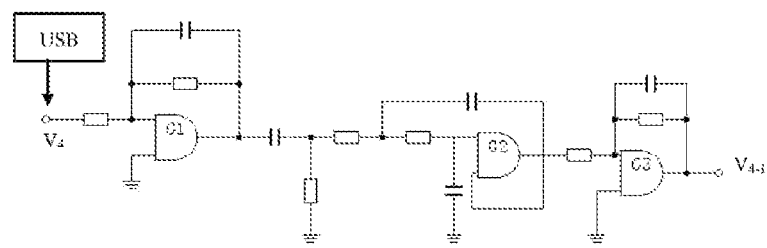
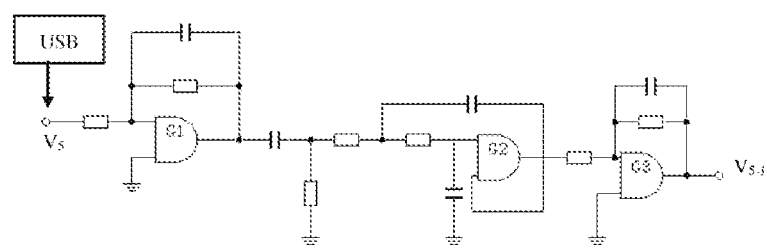

Fig.13 Signal amplification circuit

Fig.15 Flowchart

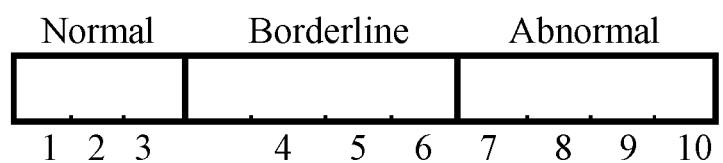
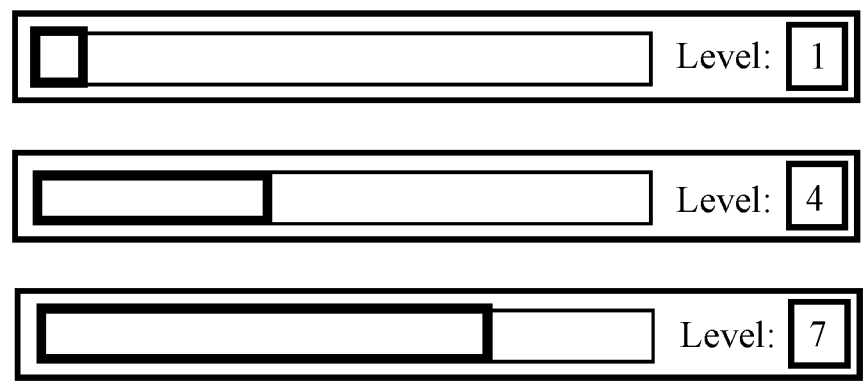
Fig. 16

CARDIOVASCULAR DETECTION SYSTEM AND METHOD

BACKGROUND OF THE INVENTION

1. Field of the Invention

The invention belongs to the field of cardiovascular detection and diagnostics. It is an invention, a method, a system, and a device. There is a variety of cardiovascular functional statuses, for a variety of cardiovascular disease detection and diagnosis. It seeks to classify heart conditions into different levels and classifications.

2. Description of the Related Art

The biological human body contains a large number of bio-electrical signals, from the heart, the brain, the gastric system, and multiple different muscles. The heart's bio-electrical information is one of the most important pieces of bio-physical information. The information is important to biological survival; if the heart's electrical information is terminally disrupted, the human body will cease to survive.

In 1903, Leiden University professor and physiologist Willem Einthoven, on the basis of previous work, successfully measured heart's electrical wave group from the heart for the first time in human history. Thus, in 1903, marked the official birth of the ECG, or electrocardiogram. Professor Einthoven was credited as the inventor of the electrocardiogram.

The momentous contribution of Professor Einthoven marked the first time in the history of mankind that the bio-electric information from the heart was measured and analyzed using a time domain-wide scientific analysis. Thus the ECG findings from the human heart was the first breakthrough in time domain analysis on the heart.

The ECG is a reflection of the heart's electrical activity; its basic function and cardiac pathology research has important reference values. For instance, the ECG can analyze and identify various arrhythmias; arrhythmias and conduction blocks have important diagnostic values. The ECG is the gold index for arrhythmia. However, it is vastly insensitive in detecting some of the most important heart diseases, such as coronary heart disease, as well as myocardial ischemia. Thus, it cannot provide reliable early diagnosis or information about dangerous and potentially fatal heart problems.

To improve the diagnostic capabilities of ECG, researchers have made great efforts, and various attempts, such as the VCG (Vectorcardiogram), the Holter, the exercise stress ECG (Stress Test), the high frequency electrocardiogram (HFEKG), the VLP (Ventricular Late Potentials), the ECG body surface potential mapping, the heart rate variability (EKG Mapping and Heart Rate Variability, HRV), and others. As briefly mentioned above, these methods provide only limited or even sometimes problematic improvement over the accuracy of the ECG. For example, the exercise stress ECG (stress Test), can improve the diagnosis of coronary heart disease by 15-20%, but it has brought more than 25% of false positives, and may induce potential myocardial infarction. Therefore, the ECG, which was invented over 100 years ago, is still the main heart disease diagnostic tool in the modern day medical field.

The ECG is essentially the analysis of cardiac electrical signals in the time domain, using time for the horizontal axis, and the amplitude of P, QRS, T waves for the vertical axis. The signals are analyzed to see if the waveforms change to determine the states of cardiac function. In fact, the body's bio-electrical signals bear extremely rich information; the ECG only utilizes the time-domain analysis aspect, and misses a lot of information via other aspects. We can gather a lot more information from other angles as well.

In the 1970-1980s, a group of Chinese experts (including the inventor) embarked upon theoretical research upon the human heart:

We set up a mathematical model of the heart by simulating the heart as being composed of two mediums: vidscoelastic substance and non-Newtonian fluid. The special moving boundary is also taken into consideration. The dynamics model of the heart is therefore established. The solution obtained through topol transformation and the combination of theory analysis with clinical practice which brings the theory into a useful new diagnostic instrument.

The Kernel of the Theory

Myocardium is viscoelastic substance corresponding to pulsing condition. When we consider heart from its structure, the heart is made up of a certain number (m) of myocardium shells. Each shell has n strips of boundary. A generalized variational function is conducted:

$$\pi^m = \int_{t_1}^{t_1+T} dt \iint_\sigma \int^{>m>m>m} \underline{h} \underline{u} ds + \sum_{n=1}^{N_m} \left\{ \int_{t_1}^{t_1+T^n} dt \int_c \left[ ^{>mn} \ell_1 \left( ^{>mn}_{\underline{u}} - \overline{\underline{u}}^{>mn} \right) \underline{u}^{>mn} \right] dl + \int_{t_1}^{t_1+T'} dt \int \left[ ^{>mn} \ell_2 \left( ^{>mn}_{\underline{u}} - \overline{\underline{u}}^{>mn} \right) \cdot \nabla_2 \underline{u}_s^{>mn>mn} \right] dl \right\} + \int_{t_1}^{t_1+T'} dt \iint_\sigma \int \left[ ^{>m}_{\underline{E}} \cdot ^{>m}_{\underline{V}'} \right] \underline{u}^{>m} \underline{T} \underline{u}'^{>m>m>m} ds \quad (m=1,2,\ldots m) \quad (1)$$

Here: > is the physical variable described by Lagrange coordinate, — stands for the physical variable on the boundary, $\underline{u}$ is the shifting vector of the myocardium shells, u, is the normal shift of the myocardium shells, v' is the speed vector of blood, $\underline{h}$ is the energy operator of the myocardium shells $\overset{\ell}{\underline{\ell}}_1 \overset{\ell}{\underline{\ell}}_2$ are the conditional operators of myocardium's boundary. $\tau_2$ is the two dimensional gradient operator. $\underline{E}$ is the exchange operator between fluid speed and trans-shape speed, ds is the surface integral infinitesimal, dl is the curve integral infinitesimal of the boundary, T' is the vibration cycle, $\underline{T}$ is the coordinate transformation operator to $\underline{u}'$, $\underline{u}'$ is the shift vector of blood, m is the number of the myocardium shells, mn is nth boundary of the mth myocardium shell.

Blood is non-Newtonian fluid, the flowage of blood in heart chambers can be expressed by the following generalized variational function.

$$\int_{t_1}^{t_1+T'} dt \iiint \left\{ \left( \frac{\partial v}{\partial \tau} - \overset{<}{\partial} \overset{<}{P} + \overset{<}{\underline{u}} \left( \overset{l_2}{v} \mu(I_2^{<}) \right) \right) g \tilde{u} dt T \right. \quad (2)$$

-continued $$\sum_{m=1}^{m} \int_{t_t}^{t_1+T'} dt \int\int_\sigma \left(\overset{<m}{v}\frac{du^{<m}}{dt}\right)\left(\overset{<m}{E}\cdot\partial\overset{<m}{v}\right)T'\cdot u'ds = 0$$

From the simplified solution of the equation above, we can draw the following conclusions:

<1> Similar dynamic output can be obtained from a certain ECG in many different conditions by different structure of any shell of the heart, that is to say, similar ECG in a definite lead may come from different heart structure. So misleading diagnosis is likely to be made while analyzing from a single lead's ECG output signal in time domain alone. It is necessary to do multi-phase analysis of two leads to get a general signal of the internal structure change of the heart.

<2> As a dynamic combination of multi-level organism, viscoelastic substance and non-Newton fluid, the heart has a feed-back effect after every periodic movement, and affects the next cycle. Thus, a single periodic movement as Einthoven mentioned does not exist. The normal ECG's "Single heart period analysis" method has a serious disadvantage. Dynamic multiple-phase information analysis should be used to compensate for the shortage and get a better diagnostic effect. It can always enclose some pathologic changes which can not be judged by conventional ECG.

<3> As a multi-level organism structure of viscoelastic substance, coupling with blood, the natural frequency of the heart has as a specific distribution. When a vibration is excited by external stimulation (as from sinus modal), the wave form (electrocardiograph) is limited by the shape of any organism and the blood characteristics of the heart to a great extent. We should get the information of the vibration frequency of each organism coupling with blood and phase change of each point to get the information of whether there is disease in each organism of the heart. But this kind of information is hard to be distinguished from time-domain signal while a better effect can be obtained by frequency-domain and phase-shift analysis. For example, phase-shift has a direct connection with the flexibility of myocardium fibre and the thickness of the heart wall. Phase-shift can reflect some important information of the sensitivity for the hearts injury.

There are two cornerstones of science in the twentieth century—quantum mechanics and the theory of relativity, the two cornerstones enable humanity to enter the atomic and space age. In quantum mechanics, on the microcosmic level, a wave is also a particle, and a particle is also a wave. Any material can be measured using frequency spectrum and each material has its own inherent frequency spectrum. The spectrum is unique for a specific material; one of a kind. As a result, the spectrum can be marked as a material indicator, also referred to as material's fingerprint.

Any wave can be dissected into a series of waves with different frequencies, due to the appearance and progress of the computer and signal processing technology.

Signals in the time domain can be transformed into an energy spectrum, technically the spectrum can be calculated through Fast Fourier Transform (FFT).

Calculating the electrical information in the heart, through FFT, and obtaining energy spectrum information of the heart and a control group of mathematical formulas is introduced to ensure that the system is in working order.

1. Power Spectrum
   Gxx (f)=Sx (f) Sx (f)*
   Gxy (f)=Sy (f) Sx (f)*
   Where Gxx (f) is auto power spectrum, G xy is cross power spectrum, Sx(f) and Sy (f) are the Fourier transformation of Cardiac electrical signals of the lead x and y, complex number, G xy (f) is the cross power spectrum of two functions of x and y (such as the signals of two different leads of electrocardiogram). Where the asterisk * represents the complex Conjugate. The output is a ratio between selected peaks so it is a unit less value.

2. Transfer Function
   (1) Amplitude of transfer function $$|H_{xy}(f)| = \frac{|G_{xy}(f)|}{G_{xx}(f)}$$

(2) Phase shift $\theta_{xy}$ (f):

$$\theta_{xy}(f) = \tan^{-1}\frac{IMAGX}{REALX}$$

$$x = \frac{G_{xy}(f)}{G_{xx}(f)}$$

Where |Hxy(f) is amplitude ratio of transfer function, θxy (f) is the phase shift. Gxy(f) is the cross power spectrum of two leads of Cardiac electrical signals, Gxx(f) is the auto power spectrum of the lead x. Vertical line represents the above mentioned diagram of amplitude frequency characteristic and phase-frequency characteristic of transfer function. The Phase Shift corresponds to the amplitude phase characteristic of transfer function, corresponds to the amplitude phase characteristic of "Bode diagram." In electrical engineering and control theory, a Bode plot is a graph of the frequency response of a system. It is usually a combination of a Bode magnitude plot, expressing the magnitude of the frequency response, and a Bode phase plot, expressing the phase shift. Both quantities are plotted against a horizontal axis proportional to the logarithm of frequency. Phase shift is two lead ECG signal phase difference. The unit of measurement is millimeters. The phase shift can be combined with other indicators to judge the different diseases. In Step 5 of the analysis the lead phase shift is indicative of normal and abnormal heart function that has been correlated to data from clinical trials.

3. Impulse Response
   Between impulse response and transfer function, their relation is a Fourier transformation. In practical application, transfer function can be obtained by the spectrum analysis of inter process signal:

$$|Hx(f)| = \frac{G_{xy}(f)}{G_{xx}(f)}$$

From the calculating expressions of impulse response, we know it responds to unit excitation at point x. The response ration excited at points x1 and x2 is represented by the expression:

$$X_2(t) = \int_{-\infty}^{\infty} lH_{x1x2}(t)\, x_1(t-\tau)d\tau$$

Impulse response is calculated to analyze two lead of Cardiac electrical signals transmission system characteristics. The unit of measurement is in millimeters. The phase shift can be combined with other indicators to judge the different diseases. The data was obtained from a large number of clinical trials.

4. Coherence

The coherence function between two leads of Cardiac electrical signals of x (t) and y (t) is:

$$\gamma xy2(f)=|G\ xy(f)|/Gxx(f)Gyy(f)$$

Because the amplitude of cross power spectrum possesses an important relation expression, i.e. inequality of cross spectrum:

$$|G_{xy}(f)|^2 \le G_{xx}(f)G_{yy}(f)$$

hence $$0 \le \frac{|G_{xy}(f)|^2}{G_{xx}(f)G_{yy}(f)} \le 1$$

Therefore the value of coherence function is between 0 and 1.

The coherence function represents coordination in different parts of the Cardiac electrical signals, the unit of measurement is millimeters. Coherence combined with other indicators can be correlated to different diseases based on clinical trials data.

5. Cross Relation

The cross correlation function of stochastic data of two variables (corresponding to the signals of two different leads of the electrocardiogram is the description of the mutual relation between the values of lead x at time t and the value of lead y at time t+τ. When expression:

$$\phi_{xy}(\tau) = \lim_{T \to \infty} \frac{1}{2T} \int_{-T}^{T} \hat{r}_x(t) \cdot f_y(t+\tau) dt$$

is applied to the analysis of Cardiac electrical signals, the meaning of each symbol is as follows: Φxy τ represents the cross correlation function of electrocardiogram, t is time, τ is time lag (or is called time delay), fy(t) and fx(t) are two leads signal of the electrocardiogram. The subscripts x and y express two different leads of Cardiac electrical signals, 2T (i.e. from −T to T) is the record time of electrocardiogram. In general, we take 2T as 3.

Cardiac electrical signals correlation is the relationship between the two leads on a different cycle time measured in millisecond per millimeter. The cross-correlation combined with other indicators can be correlated to different diseases based on clinical trials data.

This phase of the research involves using the frequency domain, instead of the time domain, for the analysis of human cardiac electrical information to improve the sensitivity of detection of myocardial ischemia. Their representatives as "The Theoretical Basis and Clinical Study of EKG Multiphase Information System" (For The American Society of Hypertension, Sixth Scientific Meeting by Dan Qun Fang et al), and by U.S. Pat. No. 5,509,425, entitled "Arrangement for and Method of Diagnosing and Warning of a Heart Attack."

However, this method also has drawbacks, transforming Cardiac electrical signals in time domain into frequency domain using the Fourier transform could only be done on 5 leads of a conventional ECG, i.e. V5 and lead II, and resulted in significant information loss. Additionally, myocardial ischemia could not be located in the heart. This being said, Dan Qun Fang and Hai Xiang Liu solved this problem. They invented a heart disease detection and location system, particularly for the detection and localization of coronary heart disease, including myocardial ischemia and myocardial infarction. The system first collected from human ECG signals, amplified and digitized them, then used the 12 leads of the power spectrum waveform recognition and high-frequency cut-off values to calculate the power spectrum of cardiac electrical signals in 12 leads obtained—the base value, low-frequency component divided by the high-frequency components, and finally, in accordance with the evaluation criteria of the size and distribution of leads, provided diagnosis of the myocardial ischemia location map. The invention improved the detection rate of coronary heart disease, the first killer of human deaths, to 90% sensitivity. This invention became U.S. Pat. Nos. 6,148,228, 6,638,232B1, 6,936,010B2, entitled "System And Method For Detecting And Locating Heart Disease." However, this invention is also flawed. First, there is no indication which one of the 3 main coronary artery has myocardial ischemia and myocardial infarction. Second, it is only divided by the integral ratio with only low frequency components of the high frequency component to determine myocardial ischemia and myocardial infarction also is not fully locatable.

Relevant Art

U.S. Pat. No. 4,974,162, entitled ADVANCED SIGNAL PROCESSING METHODOLOGY FOR THE DETECTION, LOCALIZATION AND QUANTIFICATION OF ACUTE MYOCARDIAL ISCHEMIA discloses both ECG signals into the multichannel spectrum domain, to localize Myocardial ischemia.

U.S. Pat. No. 4,974,598, entitled EKG SYSTEM AND METHOD USING STATISTICAL ANALYSIS OF HEARTBEATS AND TOPOGRAPHIC MAPPING OF BODY SURFACE POTENTIALS discloses frequency domain analysis, space-time or space-frequency factor, etc., but did not leave the ECG time domain, since the invention was carried out in the time domain cardiac electrical signal analysis, to give after QRS, do spectrum analysis, and the current invention is a direct spectral analysis of the heart's electrical signal, which is fundamentally different.

U.S. Pat. No. 5,020,540, entitled CARDIAC BIOPOTENTIAL ANALYSIS SYSTEM AND METHOD also discloses frequency domain analysis, and there are a series of three-dimensional maps. But also in the cardiac electrical signals were time domain analysis, QRS, and so after, do spectrum analysis.

U.S. Pat. No. 5,092,341, entitled SURFACE ECG FREQUENCY ANALYSIS SYSTEM AND METHOD BASED UPON OTHER PUBLICATIONS SPECTRAL TURBULENCE ESTIMATION discloses similar analysis as the above disclosed patents.

U.S. Pat. No. 5,109,862, entitled METHOD AND APPARATUS FOR SPECTRAL ANALYSIS OF ELECTROCARDIOGRAPHIC SIGNALS discloses spectral analysis.

U.S. Pat. No. 5,213,105, entitled FREQUENCY DOMAIN OPTICAL IMAGING USING DIFFUSION OF INTENSITY MODULATED RADIATION discloses frequency domain imaging using array detectors.

U.S. Pat. No. 5,217,021, entitled DETECTION OF CARDIAC ARRHYTHMIAS USING CORRELATION OF A CARDIAC ELECTRICAL SIGNALS AND TEMPORAL DATA COMPRESSION discloses sampling frequency.

U.S. Pat. No. 5,575,284 entitled PORTABLE PULSE OXIMETER discloses the Fast Fourier Transform (FFT) on the time domain data. The frequency domain data is then processed to determine the saturation value.

BRIEF SUMMARY OF THE INVENTION

The invention unites the heart's electrical information, the time domain, the frequency domain, and spatial domain under one unified method, diagnostic system, and instrument. It greatly improves the detection and diagnosis of cardiovascular function and its sensitivity and specificity.

In the present invention, a method, a system, an instrument, while the electrical signal of the heart for ECG and quantum spectrum were detected and analyzed, and a variety of diagnostic cardiovascular function and disorders.

The present invention provides: detection of mild insufficient perfusion to myocardium, insufficient perfusion to myocardium, and insufficient perfusion to myocardium. As well as the presence of a compensated hyper dynamic ventricular response; ischemia, such as different levels of cardiovascular functional status of detection and diagnosis. Myocardial ischemia gives light to heavy holographic analysis. Mankind for detection and diagnosis of myocardial ischemia enter level early prediction and severe warning.

The present invention provides calculates and outputs poor conduction function, poor systemic blood circulation, change of blood dynamics, left ventricular dysfunction, high voltage in the left ventricle, prior injury to the myocardium, arrhythmia, adverse cardiovascular function testing and diagnosis.

The present invention with a combination of different indicators and large number of clinical trials allows for accurate coronary heart disease, myocardial infarction, ventricular hypertrophy, pulmonary heart disease, small vessel disease, chronic blood disease, congenital heart disease, atrial fibrillation, ventricular arrhythmia, supraventricular arrhythmia, congestive heart failure, dilated cardiomyopathy detection and diagnosis. Under one unified method, diagnostic system, and instrument.

The present invention allows for coronary heart disease, myocardial infarction location detection and diagnosis, and not only the typical position, but also where in the three main coronary arteries it occurs.

The present invention uses quantum spectrum analysis of the heart's electrical information, comprehensive ECG temporal, spatial domain VCG, and reference to cardiac risk factors. It also presents the concept of a human heart level; from normal human heart, sub-health, to patient, critically-ill patient, and further divided into 10 levels. Given the level of the human heart health quantify under one unified method, diagnostic system, and instrument. This allows the improved detection and diagnosis of heart disease and conditions. The invention provides detection and diagnosis of the human heart health with early diagnosis and provides preventive medicine.

An object of the invention is to focus on time domain, frequency domain, spatial domain fusion unified in a way, a diagnostic system to make the analysis of human cardiac electrophysiology information reaches a three dimensional holographic analysis level.

An object of the invention is to utilize the most useful indicators of effective quantum spectrum of cardiac electrical signal, the most effective diagnostic index ECG time domain fused together to form a set of electrical signals to the heart of the new holographic analysis of diagnostic index capable of diagnosing coronary heart disease, myocardial infarction, ventricular hypertrophy, pulmonary heart disease, small vessel disease, chronic blood disease, congenital heart disease, atrial fibrillation, ventricular arrhythmia, supraventricular arrhythmias, congestive heart failure, dilated cardiomyopathy.

An object of the invention is to create a simple and useful five sections; namely, (1) First section—normal amount of perfusion to myocardium; (2) Second section—mild deficit perfusion to myocardium; (3) third section—moderate deficit perfusion to myocardium; (4) Fourth section—severe perfusion deficit to myocardium; (5) Fifth section—ischemia. This allows for the earlier detection of ischemia without the need to perform invasive angiography.

It is an object of the present invention to determine which of the three main coronary arteries impacts myocardial ischemia and myocardial infarction without performing invasive angiography.

It is an object of the invention to analyze the integral ratio of high frequency to low frequency component and P21, P51 combination to assess myocardial ischemia or myocardial infarction and to rotate 3D stereoscopic display of the heart and the affected area.

It is an object of the present invention to create a scale of one to ten to overlay the four levels described above as normal health, sub-health, the beginning of heart stress, and critically ill patients.

Another objective of the present invention while the electrical signal of the heart for ECG and quantum spectrum were detected and analyzed, and a variety of diagnostic cardiovascular function and disorders, under one unified method, diagnostic system, and instrument.

ECG's time domain of more than 100 years ago, is still the "gold standard" of arrhythmia detection, but its low sensitivity renders it largely useless for detecting myocardial ischemia. The inventor's frequency domain analysis, can be the "gold standard" of myocardial ischemia detection. The inventor looks to combine both systems in one instrument, the ECG analysis in time domain and frequency domain, allowing the system and the newly invented instrument, for the optimal overall cardiac function analysis and diagnosis, so that this new system can become the new "gold standard" in both myocardial ischemia and arrhythmia detection, and will hopefully be a major breakthrough in the modern analysis of cardiac electrical information.

The manners in which the invention achieves its objects and other objects which are inherent in the invention will become more readily apparent when reference is made to the accompanying drawings wherein like numbers indicate corresponding parts throughout.

BRIEF DESCRIPTION OF THE DRAWINGS

FIG. 1 shows block diagram showing the composition of the various parts of the cardiovascular system for the detection, diagnosis and localization method, system and instrument of the present invention.

FIG. 2 shows simplified graphical depiction of the 12-lead lead wire connected to each respective position on the body.

FIG. 3 shows a 12-lead ECG cable pattern.

FIG. 4 shows simplified graphical depiction of the 12-lead ECG

FIG. 5 shows simplified graphical depiction of each wave, segment, and interval in the electrocardiogram.

FIG. 7A shows simplified graphical depiction of a Phase Shift schematic of cardiac electrical signals in the quantum power spectrum between dual leads.

FIG. 7B shows simplified graphical depiction of an Impulse Response schematic of cardiac electrical signals quantum power spectrum between dual leads.

FIG. 7C shows simplified graphical depiction of a Cross Correlation schematic of cardiac electrical signals quantum power spectrum between dual leads.

FIG. 7D shows simplified graphical depiction of a Coherence schematic of cardiac electrical signals quantum power spectrum between dual leads.

FIG. 8 shows depiction of the basing of the value of f0 as a division of the cardiac electrical schematic diagram of the quantum power spectrum.

FIG. 9 shows simplified graphical depiction of the frontal and lateral surfaces of the lead distribution and location map of the evaluation standard.

FIG. 11A shows front view diagram in which you can see the left anterior descending artery (LAD) and its branch vessels, and the right coronary artery (RCA) and its branch vessel disposal.

Section 11B shows rear view diagram in which you can see the circumflex artery (LCX) and its branch vessels.

Figure 12A:

FIG. 12A shows 1-3, normal, healthy person, with green.

Figure 12B:

FIG. 12B shows 4-6, borderline, sub-healthy group, with yellow.

Figure 12C:

FIG. 12C shows 7-8, abnormal heart health and the heart shows signs of cardiovascular diseases, with orange.

Figure 12D:
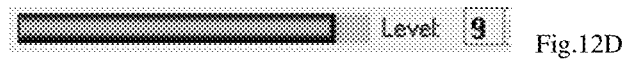

FIG. 12D shows 9-10, myocardial infarction, sudden death or cardiac risks. Shown in red.

Figure 13:
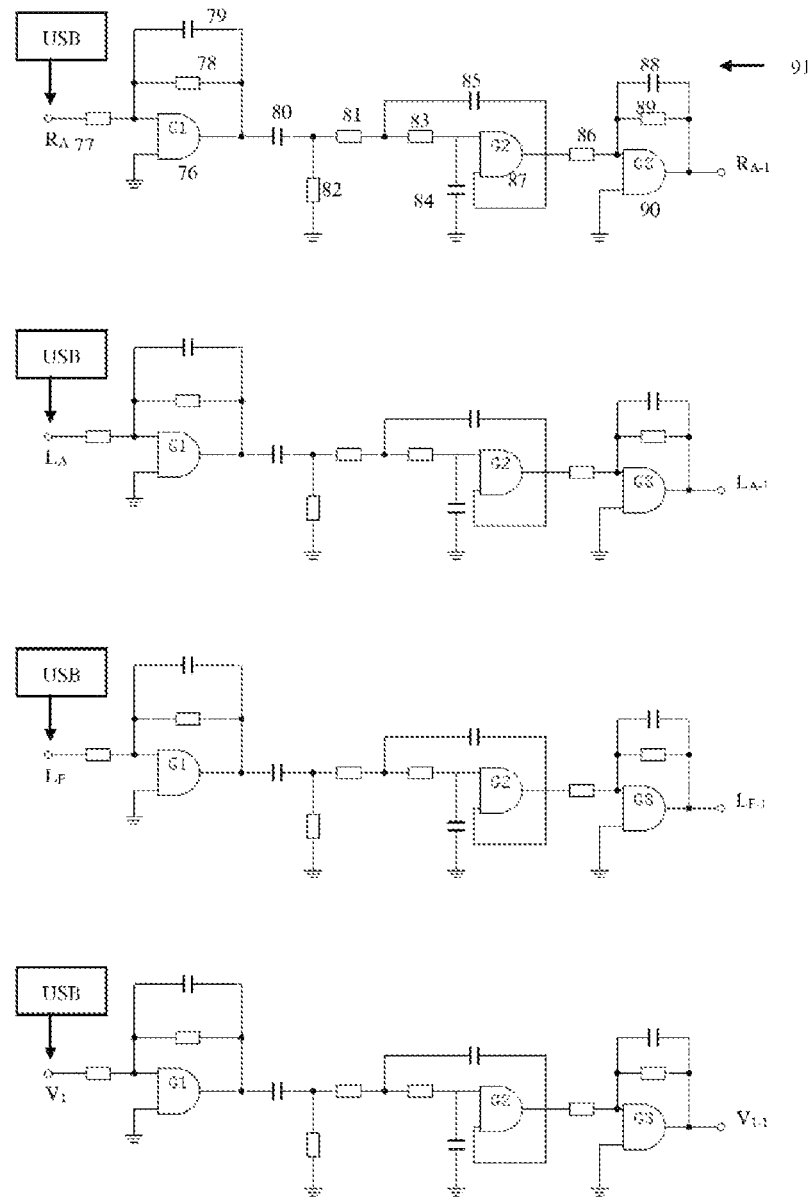
Figure 13:
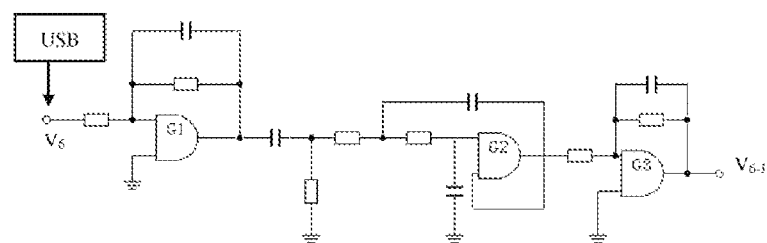

FIG. 13 shows an amplification circuit for the present invention, comprising three (3) pages.

Figure 14:
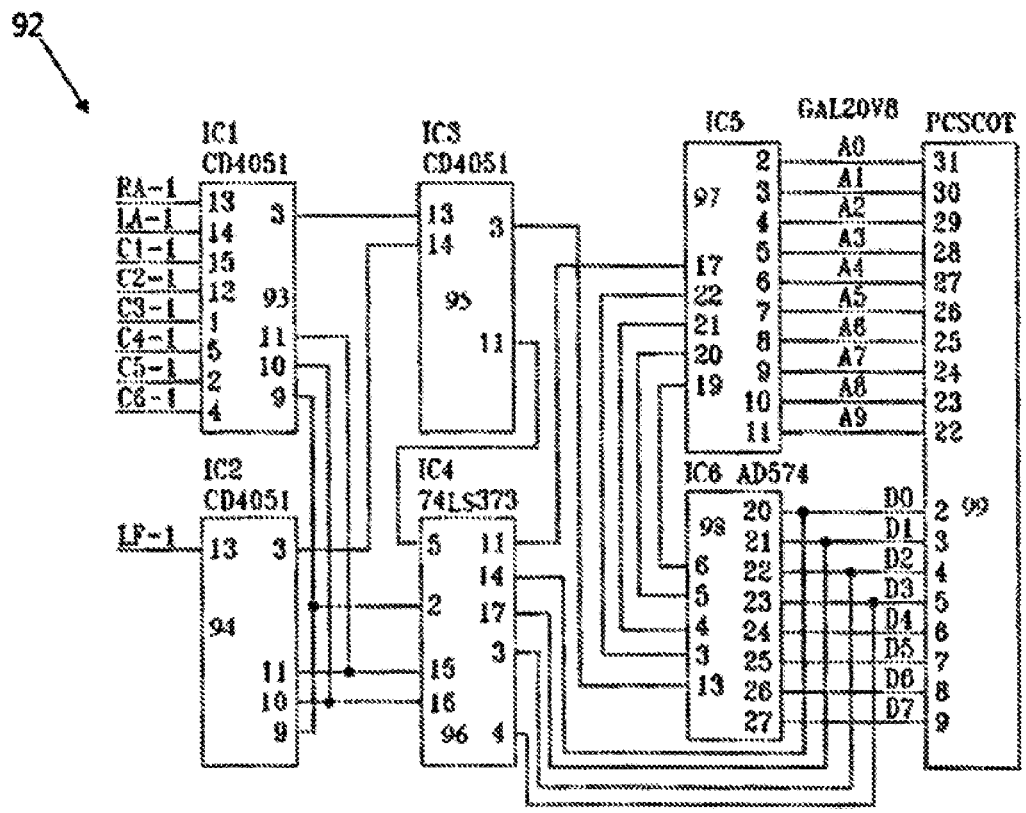

FIG. 14 shows circuit diagram of ECG analog to digital conversion.

Figure 15:
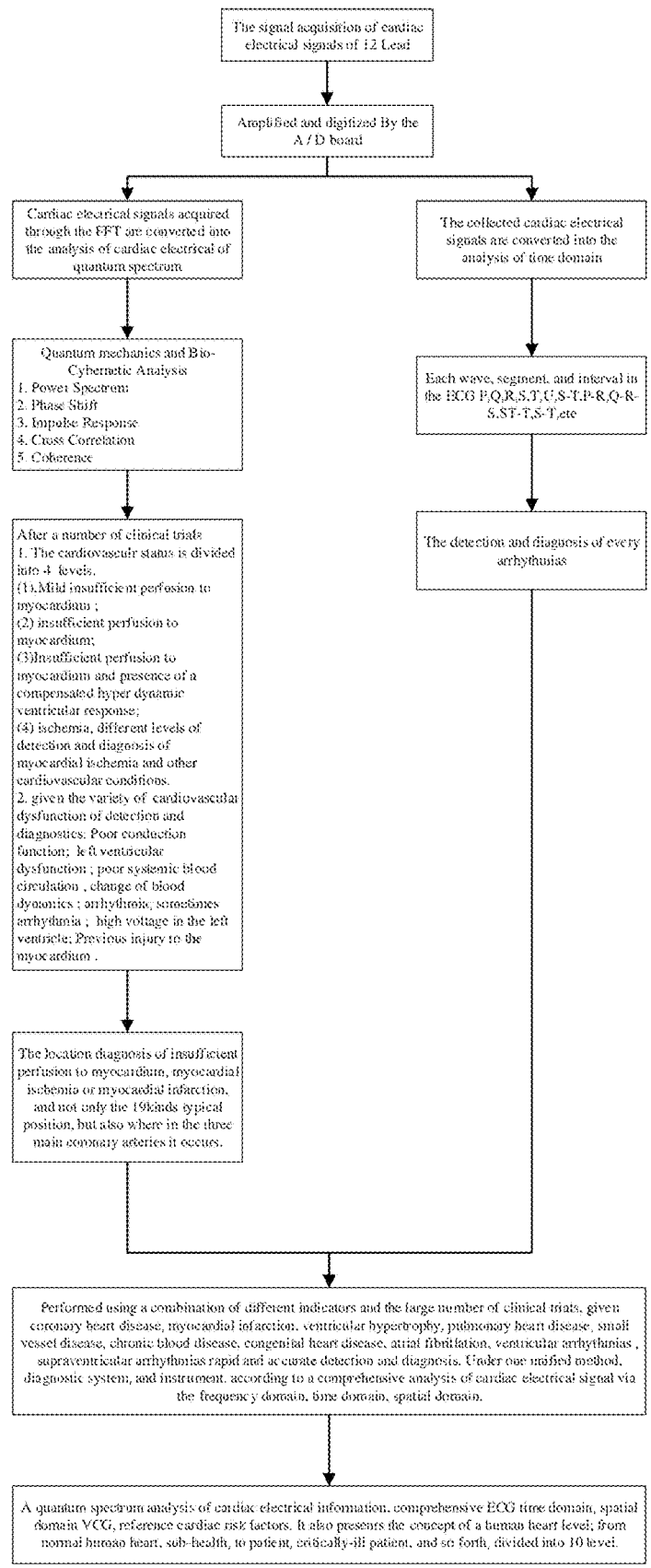

FIG. 15 is each part of the flowchart in the present invention of an application of cardiac electrical signal via the frequency domain, time domain, spatial domain, and the detection and diagnosis of a variety of cardiovascular disorders and level of heart condition; this shows comprehensive analysis using novel methods, systems and instrument.

DETAILED DESCRIPTION OF THE INVENTION

A method for detecting, diagnosing and locating function and disorders of the cardiovascular system of the present invention provides a system, and gives a detection level of the human heart, in seven steps.

The first step is the signal acquisition of cardiac electrical signals using ECG leads placed on the body's surface, including the position of the electrode of the right arm (RA), left arm (LA), right (RL), left (LL) and the six chest positions (V1, V2, V3, V4, V5, V6).

| Electrode name | Electrode placement |
|---|---|
| RA | On the right arm, avoiding thick muscle. |
| LA | In the same location where RA was placed, but on the left arm. |
| RL | On the right leg, lateral calf muscle. |
| LL | In the same location where RL was placed, but on the left leg. |
| $V_1$ | In the fourth intercostal space (between ribs 4 and 5) just to the right of the sternum (breastbone). |
| $V_2$ | In the fourth intercostal space (between ribs 4 and 5) just to the left of the sternum. |
| $V_3$ | Between leads $V_2$ and $V_4$. |
| $V_4$ | In the fifth intercostal space (between ribs 5 and 6) in the mid-clavicular line. |
| $V_5$ | Horizontally even with $V_4$, in the left anterior axillary line. |
| $V_6$ | Horizontally even with $V_4$ and $V_5$ in the midaxillary line. |

The second step is the collection of the heart's electrical signals by the A/D board, and afterwards amplified and digitized. The A/D board includes over 5000V of isolated voltage to ensure personal safety.

The third step is the analysis of the collected cardiac electrical signals. First, the collected cardiac electrical signals are used to calculate time domain signal of the standard lead, a standard lead time domain signal including at least one of the 12 leads, 12-lead ECG is I lead, II lead, III lead, aVR lead, AVL lead, aVF lead, V1 lead, V2 lead, V3 lead, V4 lead, V5 lead, V6 lead. Each analysis leads online form and rhythm, gives Heart Rate, P Duration, PR Interval. QRS Duration, QT Interval, QTc Interval, P Axis, QRS Axis, T Axis, and P+, P, Q, R, S, J, ST20, ST40, ST60, ST80, T+, T. and the like. Second, the cardiac electrical signals acquired through the FFT are converted into a power spectrum signal, standard lead frequency domain signal comprises at least one a of 12-lead, 12-lead is I lead, II lead, III lead, aVR lead, AVL lead, aVF lead, V1 lead, V2 lead, V3 lead, V4 lead, V5 lead, V6 lead. At the same time, in order to calculate and analyze the heart, we assume that V4 lead, V5 lead, V6 lead of chest guide as the input signal, and the standard I lead, II lead, III lead of limb leads of as an output signal, we can obtain between the two signals (double leads of the phase shift, impulse response, cross correlation and coherence. At least one pair leads, such as between the between I lead and V4 lead or between II lead and V5 lead, or between III lead and V6 lead and comparison between many dual lead pairs. This defines the analysis of cardiac electrical of quantum spectrum analysis.

The fourth step is the result of a large number of clinical trials, the selection of a series of diagnostic indicators of quantum spectrum of practical 12-lead cardiac electrical signals and combined into an overall detection and diagnosis for a variety of cardiovascular function and a variety of comprehensive cardiovascular disease detection and diagnosis. These indicators are P21 (second peak is greater than the first peak), P43 (fourth peak is greater than the third peak), P51 (fifth peak is greater than the first peak), P53 (fifth peak is greater than the third peak), L01 (the first peak is too low), L03 (third peak is too low), L0A (Average amplitude of first four peaks too low); HAP (Average amplitude of first four peaks too height), PHS (great deviations and fluctuations of phase shift), MPI (main peak of impulse response is inverted), WMP (wide multiple main peaks or a plurality in impulse response), SWP (bilateral distant sinusoidal waves on both sides of the main peak (wing sub-responses) of impulse response), USW (bilateral immediate responses on both sides close to main peak (immediate sub-response) of impulse response), MPL (the main peak of cross correlation is too low), MPH (the main peak of cross correlation is too high), PCI (first main peak of cross correlation is inverted), PCL1 (the first peak of coherence is too low), PCL2 (The peak of coherence is too low after 4 Hz.).

After a number of clinical trials, the cardiovascular status from mild insufficient perfusion to myocardium ischemia, is divided into four levels, namely mild insufficient perfusion to myocardium; moderate insufficient perfusion to myocardium; significant insufficient perfusion to myocardium and presence of a compensated hyper dynamic ventricular response; and ischemia, different levels of detection and diagnosis of myocardial ischemia and other cardiovascular conditions. And evaluation correspond to: (1) Mild insufficient perfusion to myocardium—P43, P53; (2) insufficient perfusion to myocardium—P21, L0A; (3) insufficient perfusion to myocardium and presence of a compensated hyper dynamic ventricular response—P51; and (4) Myocardial Ischemia—P21 and P51 of the composite; P21, P51 and PHS, MPI compound; P21, P51, and the composite L0A; given mild to severe myocardial ischemia of varying degrees of holographic analysis. And ischemia of varying degrees of light to heavy detection and diagnosis.

After a number of clinical trials, given the variety of cardiovascular dysfunction of detection and diagnostics: poor conduction function—MPI; left ventricular dysfunction—WMP; poor systemic blood circulation, change of blood dynamics—PHS; arrhythmia—USW; sometimes arrhythmia—PCL1, PCL2; high voltage in the left ventricle—MPH; previous injury to the myocardium—L01, L02 have now been correlated.

After a number of clinical trials, all of these indicators can be combined in order to detect the degree of ischemia the cardiovascular status from mild myocardial insufficiency perfusion to moderate insufficiency to myocardium to myocardium ischemia. The range from mild myocardial insufficiency perfusion to moderate insufficiency to myocardium to myocardium ischemia is divided into five sections, an ischemia index 0-IV, degree of perfusion to myocardium 0-100%) namely, (1) First section—normal amount of perfusion to myocardium (ischemia index 0, not ischemia); (2) Second section—mild insufficient perfusion to myocardium (ischemia index I, degree of perfusion to myocardium 1-25%); (3) third section-moderate insufficient perfusion to myocardium (ischemia index II, degree of perfusion to myocardium 25-50%); (4) Fourth section-severe insufficient perfusion to myocardium (ischemia index III degree of perfusion to myocardium 50-75%); at this time, cardiac insufficiency starts making compensation mechanism, the heart has begun to use extra energy; (5) Fifth section—ischemia (ischemia index IV, degree of perfusion to myocardium 75-100%). The 5 section and diagnostic indicators are (1) the first section is normal perfusion to myocardium and every indicator normal in cardio quantum spectrum, or individual indicator appear "+" in the cardio quantum spectrum diagnostic indicators but (a) R21, R51 cannot have the "+," (b) double lead of MPI, WMP, SWP, PHS, MPL, MPH, PCI's any one cannot have the "+." (2) Second section—mild insufficient perfusion to myocardium—P43, P53 combinations. (3) third section—moderate insufficient perfusion to myocardium—P21, LOA and combinations thereof, for example, where the P21 in II, V5, there is a "+" appears, together with other leads in three a "+," the sentence is: "moderate insufficient perfusion to myocardium;" where the P21 in II, V5 in both a "+," the sentence is: "moderate insufficient perfusion to myocardium;" where the P21 in addition to other leads II, V5 outside in 6 The "+," the sentence is: "moderate insufficient perfusion to myocardium." Where LOA "+" The total is greater than 5, then ruled: "moderate insufficient perfusion to myocardium;" where the LOA "+" The total is more than 3, together with other three leads in a "+," the sentence is: "moderate insufficient perfusion to myocardium;" where the LOA "+" The total is more than 3, P21 in addition to other leads II, V5 has three outside a "+," the sentence is: "moderate insufficient perfusion to myocardium." (4) Fourth section—severe insufficient perfusion to myocardium—P51, P21, LOA combination. (5) Fifth section—myocardial ischemia—P21, P51, PHS, MPI composite, for example, P21, P51 of II lead and V5 lead all "+" (abnormal), compared with myocardial ischemia; 12 lead P21, P51's 24 index-linked in 16 and 16 above is "+," compared with myocardial ischemia; P21, P51 and PHS, MPI composite, for example, P21, P51 has 10 or more for the "+," plus MPI, PHS two indicators have one for "+" can be judged as myocardial ischemia.

P43, P53, P21, P51, LOA, MPI, PHS complex; gives an analysis of myocardial ischemia of varying degrees from lighter to heavier and the detection and diagnosis of ischemia of varying degrees. A series of diagnostic indicators of quantum spectrum in the detection and diagnosis of the history of myocardial ischemia, featuring of the present invention is a practical 12 lead cardiac electrical signals, combined into an overall detection and diagnosis, in a way, a system, an instrument a time of myocardial ischemia lighter to heavier degree, carried out detection and diagnosis. The system yields accurate and rapid direct non-invasive detection and diagnosis of myocardial ischemia, and myocardial ischemia distinguish severity. Because of this technology, it opens up "real-time" monitoring (especially before and after surgery), doctors "efficacy," and "real-time" detection.

The fifth step is performed using a combination of different indicators and the large number of clinical trials, given coronary heart disease, myocardial infarction, ventricular hypertrophy, pulmonary heart disease, small vessel disease, chronic blood disease, congenital heart disease, atrial fibrillation, ventricular arrhythmias, supraventricular arrhythmias, Congestive heart failure (CHF), dilated cardiomyopathy (DCM) rapid and accurate detection and diagnosis. Coronary heart disease—P21, P51, LOA, MPI, PHS, mutual combinations; MI—P21, P51, LO1, L02, MPI, PHS, SWP, MPL, mutual combinations; ventricular hypertrophy—HAP MPH combination with each other and; pulmonary heart disease—P21, P51 and MPH (V1, III, aVL lead anomalies) in combination with each other; small vessel disease—PHS and P43, P53 combined with each other; chronic blood disease—P21, P51, P43, P53 and MPL, PHS combined with each other; AF (Fibrillation)—ECG, P wave disappeared, a small f-wave frequency is 350-600 beats/min. Cardiac electrical quantum spectrum USW unusual, both in combination with each other; ventricular arrhythmia—ECG, ventricular premature contraction, ventricular tachycardia, ventricular fibrillation (VF) and ventricular flutter (VEL). Cardiac electrical quantum spectrum PL1, PL2 unusual, both in combination with each other; supraventricular arrhythmias—ECG, supraventricular tachycardia, atrial-ventricular node reentrant tachycardia, atrial-ventricular reentrant tachycardia, atrial-tachycardia. Cardiac electrical quantum spectrum PL1, PL2 unusual, both in combination with each other or both in combination with each other. Congestive heart failure (CHF)—P21, P51, WMP,USW and arrhythmia in ECG combination with each other dilated cardiomyopathy (DCM) P21, P51,LOA,LO1,LO2,HAP and QRS in ECG combination with each other.

The sixth step is location diagnosis of insufficient perfusion to myocardium, myocardial ischemia or myocardial infarction. The 12-lead into the frontal surfaces six leads (I lead, II lead, III lead, aVR lead, AVL lead, aVF lead) and horizontal surfaces 6 leads (V1 lead, V2 lead, V3 lead, V4 lead, lead V5, V6 lead) evaluation standard for each of lead (frontal surfaces and horizontal surfaces) to draw a histogram, leads the heart of their representatives in accordance with the arrangement in order, in order to facilitate observation leads adjacent evaluation standard, each histogram a representation leads to repeat. According to different combinations of leads, there are location diagnosis of 19 separate locations, and those 19 locations correspond to the combination of those leads in the following table:

factor to the heart rate to obtain the base value. The conversion factor is a constant, between 3-7, usually take 5. Evaluation standard was in the quantum power spectrum of graph, with the dividing line between high and low frequency of base value, used to divide the given quantum power spectrum into low frequency and high frequency areas. If the total area integrating of all the peaks in the low frequency area integrating (area No. 1) is greater than the total area integrating of all the peaks in the high frequency area (area No. 2) the heart is normal. On the contrary, if the total area integrating of all the peaks in the low frequency area integrating (area No. 1) is lower than the total area integrating of all the peaks in the high frequency area (area No. 2) then there is an indication of ischemic heart disease. A full description of this step is provided in U.S. Pat. No. 6,148,228. Further, the information creates a 3D rendering of the heart and graphically using color show where there is insufficient perfusion, damage, or clogging of arteries also called a 3D localization map. The display can be rotated to show the whole surface of the heart and the physician and patient can view and discuss. The physician can give an immediate assessment that the patient can understand.

If the histogram which leads more than the midline, it means that this leads abnormal, different combinations of abnormal leads, showing different parts of the heart of insufficient perfusion to myocardium, myocardial ischemia or myocardial infarction. The localization index chart localizes the insufficient perfusion to myocardium, myocardial ischemia or myocardial infarction. When only one or two columns extending down to the abnormal zone, it has no clinical significance. Only when three or four columns extending down to the abnormal zone indicates ischemia secondary to coronary artery obstruction. The degree of severity corresponds to the depth of the columns extending down into the abnormal zone. The corresponding leads along which the columns extend down into the abnormal zone denote the affected area.

Found in clinical practice that the evaluation criteria using the base value of the area integral was missing some important information. The present invention further combines anomaly evaluation criteria using the base value of the area integral with the P21, P51, and in this way obtains more

| | LOCATING STANDARDS | Locations of insufficient perfusion to myocardium, myocardial ischemia or myocardial infarction |
|---|---|---|
| 1. | V1 + V2 + V3 + V4 | Anteroseptal |
| 2. | V2 + V3 + V4 + V5 | Anterior |
| 3. | II + aVF + V1 + V2 | Inferior posterior |
| 4. | I + aVL + V3 + V4 + V5 + V6 | Antero-lateral |
| 5. | I + aVL + V5 + V6 | Lateral |
| 6. | I + aVR + aVL + V6 | Lead I area |
| 7. | II + aVR + aVF | Lead II area |
| 8. | II + aVL + aVF | Lead III area |
| 9. | I + II + aVR + V5 | Lead aVR area |
| 10. | I + III + aVL | Lead aVL area |
| 11. | II + III + aVF | Lead aVF area |
| 12. | V1 + V2 + V6 | Lead V1 area |
| 13. | V1 + V2 + V3 | Lead V2 area |
| 14. | V2 + V3 + V4 | Lead V3 area |
| 15. | V3 + V4 + V5 | Lead V4 area |
| 16. | V4 + V5 + V6 | Lead V5 area |
| 17. | V1 + V5 + V6 | Lead V6 area |
| 18. | V1 + V2 | Sepal |
| 19. | II + aVF | Inferior |

Figure 10A:
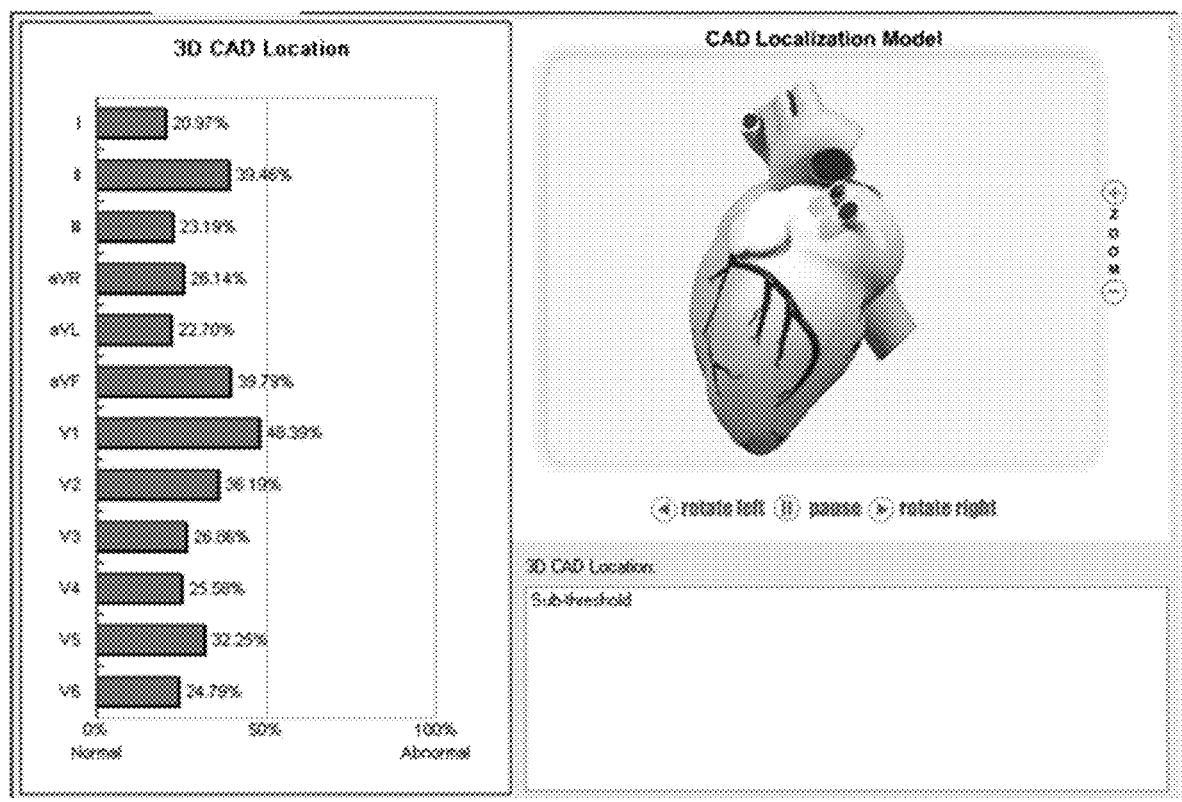
FIG. 10A shows picture of a normal, healthy person's heart and lead detection responses.
Figure 10B:
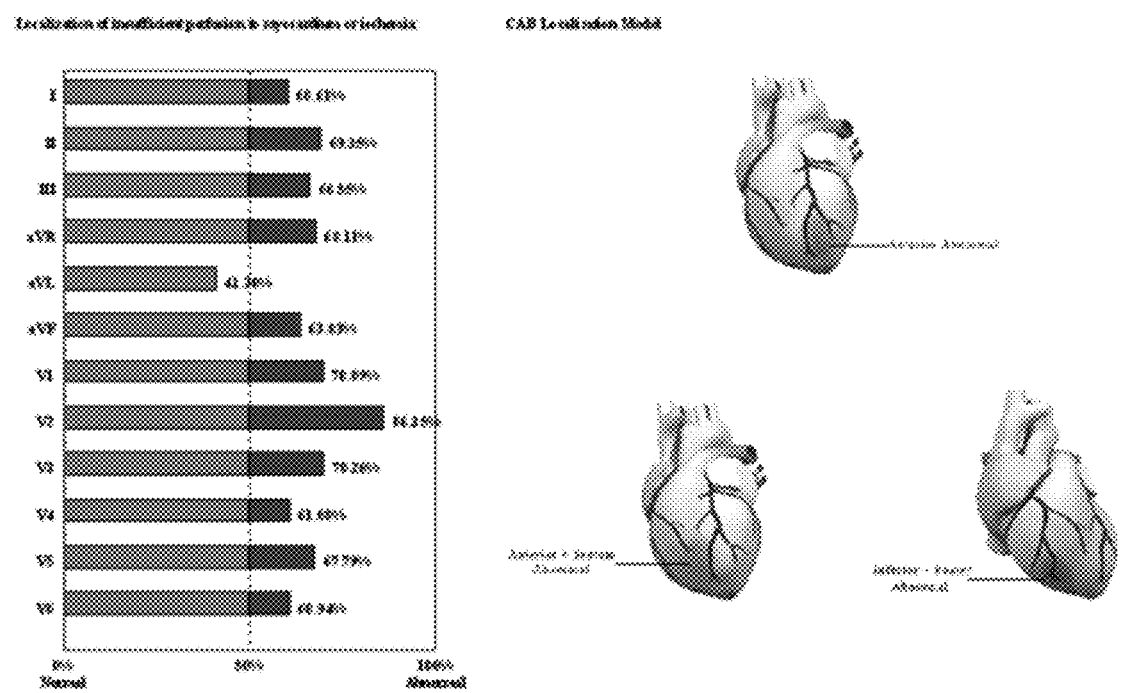
FIG. 10B shows picture of myocardial ischemia in patients with CAD.

Referring to FIGS. 10A and 10B, the heart rate is obtained to establish a base value and then the measurement of the heart rate is converted to Hertz, and applying a conversion accurate targeting criteria. And using a rotating 3D stereoscopic mode of the heart, one can visualize insufficient perfusion to myocardium, myocardial ischemia or myocardial infarction position, which on the 3D model appears red, as shown. Physicians and patients can directly see the specific location of insufficient perfusion to myocardium, myocardial ischemia or myocardial infarction.

For example, the present invention uses, in addition to the base value of the evaluation criteria of the integration of the area, the individual or P21 and P51 combination, as evaluation criteria. If the leads on P21, P51, or P21 and P51 combination go past the 50% mark in the red (abnormal) area, it means that the leads are abnormal, different, and this shows different parts of the heart having insufficient perfusion to myocardium, myocardial ischemia or myocardial infarction. When only one or two direct pairings move to the abnormal area experience stretching, there is no clinical significance. Only when the three or four pairings directly extend to the abnormal area, that it indicates the presence of myocardial ischemia, and coronary occlusion may also occur. The status of the 19 different leads correspond to the 19 different locations on the heart that may have myocardial ischemia or myocardial infarction.

The present invention further identifies for three major coronary occlusion site.

1. The left anterior descending artery (LAD) artery and its branch vessels;
2. The right coronary artery (RCA) and its branch vessels; and,
3. The left circumflex (LCX) and its branch vessels.

The location assessment for the arteries is as follows:

1. Insufficient perfusion to myocardium, myocardial ischemia or myocardial infarction of the left anterior descending artery (LAD) and its branches vessels If the following combinations show abnormal, then insufficient perfusion to myocardium, myocardial ischemia or myocardial infarction of the left anterior descending artery (LAD) and its branches vessels is detected:

| | | |
|---|---|---|
| (1) V1 + V2 + V3 + V4 | --- | Anteroseptal |
| (2) V2 + V3 + V4 + V5 | --- | Anterior |
| (4) I + aVL + V3 + V4 + V5 + V6 | --- | Anterolateral |
| (5) I + aVL + V5 + V6 | --- | Lateral |
| (10) I + III + aVL | --- | aVL area |
| (12) V1 + V2 + V6 | --- | V1 area |
| (13) V1 + V2 + V3 | --- | V2 area |
| (14) V2 + V3 + V4 | --- | V3 area |
| (15) V3 + V4 + V5 | --- | V4 area |
| (16) V4 + V5 + V6 | --- | V5 area |
| (17) V5 + V6 + V1 | --- | V6 area |
| (18) V1 + V2 | --- | Septal |

2. Insufficient perfusion to myocardium, myocardial ischemia or myocardial infarction of the right anterior descending artery (RCA) and its branches vessels If the following combinations show abnormal, then insufficient perfusion to myocardium, myocardial ischemia or myocardial infarction of the right anterior descending artery (RCA) and its branches vessels is detected:

| | | |
|---|---|---|
| (1) V1 + V2 + V3 + V4 | --- | Anteroseptal |
| (2) V2 + V3 + V4 + V5 | --- | Anterior |
| (4) I + aVL + V3 + V4 + V5 + V6 | --- | Anterolateral |
| (5) I + aVL + V5 + V6 | --- | Lateral |
| (10) I + III + aVL | --- | aVL area |
| (12) V1 + V2 + V6 | --- | V1 area |
| (13) V1 + V2 + V3 | --- | V2 area |
| (14) V2 + V3 + V4 | --- | V3 area |

3. Insufficient perfusion to myocardium, myocardial ischemia or myocardial infarction of the left circumflex artery branch vessels (LCX) and its branches vessels If the following combination show abnormal, then insufficient perfusion to myocardium, myocardial ischemia or myocardial infarction of the left circumflex artery branch vessels (LCX) and its branches vessels is detected:

(5) I+aVR+aVL+V6--- I area

The seventh step is a quantum spectrum analysis of cardiac electrical information, comprehensive ECG time domain, spatial domain VCG, and reference cardiac risk factors.

It also presents the concept of a human heart level; from normal human heart, sub-health, to unhealthy patient, critically-ill patient, and so forth, divided into 10 level. This allows the improved detection and diagnosis of heart disease and conditions.

The heart health state is divided into 10 levels (see FIG. 16).

1-3 grade, Normal, healthy person, with green.

4-6 grade, Borderline, sub-health group, with yellow. Among them, 4 sub-healthy people close to healthy, 6 sub-health people close to being a patient.

7-8 level, Abnormal, has entered cardiovascular disease, orange display, wherein, 7 light, 8 heavier.

9-10 level, myocardial infarction, sudden death or cardiac risks. Shown in red.

Detailed Explanation:

(1) Levels 1-3: healthy people.

Level 1, completely normal healthy people. Heart quantum spectrum diagnosis is normal, ECG diagnosis is normal, without any risk factors;

Level 2, although they are still normal, healthy people, but in the heart of the quantum spectrum of eight major indicators (P21, P43, P53, P51, L01, L03, L0A, HAP), there is a non-important indicator of individual appearance "+."

FIG. 16 is a graphical representation of the heart health state.

Level 3, although they are still normal, healthy people, but is already close to the sub-health level, such as may occur, mild insufficient perfusion to myocardium. High voltage in the left ventricle, previous myocardial injury or scarring in addition to the indications in Level 2.

(2) Levels 4-6: borderline health.

Level 4 of the sub-healthy people are close to healthy people but detection of insufficient perfusion to myocardium or detection of conduction abnormality or poor systematic blood circulation and change in blood dynamics are detected.

Level 5 is a standard of sub-health people, when there is insufficient perfusion to myocardium and presence of compensated hyperdynamic ventricular response.

Level 6 sub-healthy people are close to being admitted as a patient. Detection occurs when abnormal double lead index (MPI, WMP, PHS, MPL, MPH, PCI) has two "+."

(3) Level 7-8: abnormal and the heart has entered the early stages of cardiovascular disease.

Level 1-7 detects CAD; ventricular hypertrophy; pulmonary heart disease; congenital heart disease; small vessel disease; chronic blood disease; atrial fibrillation; ventricular arrhythmia; supraventricular arrhythmias, congestive heart failure (CHF), dilated cardiomyopathy (DCM).

Level 8 unhealthy people, detects the Levels 1-7, described above, each concurrent and with risk factors such as hypertension, high cholesterol, diabetes, smoking, family history of heart disease, typical angina, and atypical angina in combination with each other. Level 8 also includes detection of CAD and diabetes; CAD plus Ischemia, coupled with high blood pressure, high cholesterol, typical angina; CAD plus ventricular hypertrophy; CAD plus pulmonary heart disease; CAD plus congenital heart disease, etc., are the 8 level.

(4) Levels 9-10: critically ill patients.

Level 9 detects CAD and myocardial infarction merger.

Level 10 detects CAD merger myocardial infarction and atrial fibrillation. The patient is at risk of sudden cardiac death.

Detection, diagnosis and localization of the perfusion of the cardiovascular system and method according to the present invention sampling time takes approximately 90 seconds. The total procedural time does not exceed 10 minutes, and afterwards, the patient receives a variety of detection and diagnosis with the results as described above in a simple and intuitive format.

FIG. 1 refers to the comprehensive analysis of cardiac electrical signal in the frequency domain, the time domain, and the spatial domain, according to the current invention. It is a method, system, and instrument of detection and diagnosis of a variety of cardiovascular disorders and comprehensive analysis of the spatial domain. From body 2, cardiac electrical signals are collected by lead wire 15 and reaches the A/D amplification and digitization module 3, the A/D circuit is detailed in FIGS. 10A, 10B and 11. The cardiac electrical signal is then digitized and then entered into the computer 4.

FIG. 2 refers to the 12-lead lead wire connected to the correct positions on the body; the ECG lead is placed on the surface of the body, including the chest position of the electrode; 6 positions 5 (V1), 6 (V2), 7 (V3), 8 (V4), 9 (V5), 10 (V6), and the right arm 11 (RA), left arm 12 (LA), right foot 13 (RL), the left foot 14 (LL).

FIG. 3 refers to the 12-lead ECG cable pattern 15.

FIG. 4 refers to the 12-lead ECG schematic time domain 16, the abscissa represents the time, in seconds, and the ordinate represents the amplitude, millivolts. 17 (I lead), 18 (II lead), 19 (III lead), 20 (aVR lead), 21 (AVL lead), 22 (aVF lead), 23 (V1 lead), 24 (V2 lead), 25 (V3 lead), 26 (V4 lead), 27 (V5 lead), and 28 (V6 lead).

FIG. 5 refers to the simplified graphical depiction of each wave, segment, and interval in the electrocardiogram of 29. 30 (P-wave), 31 (Q-wave), 32 (R-wave), 33 (S-wave), 34 (T-wave), 35 (U wave), 36 (PR segment), 37 (ST segment), 38 (PR interval), 39 (Q-R-S interval), 40 (Q-T interval), 41 (S-T interval).

Figure 6A:
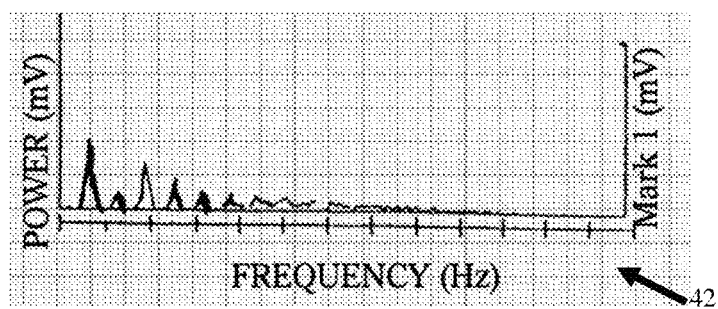
FIG. 6A of the graph is the standard normal cardiac electrical quantum power spectrum.

FIG. 6A (42) refers to the standard normal cardiac electrical signal quantum power spectrum.

Figure 6B:
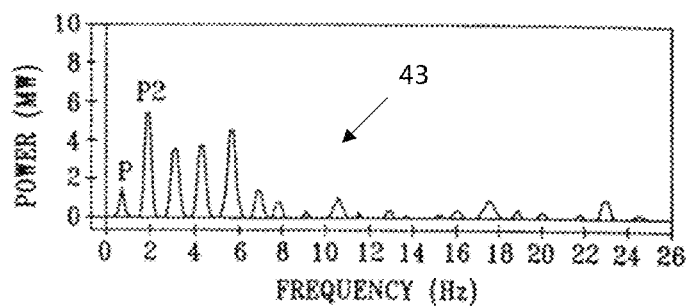
FIG. 6B shows simplified graphical depiction of the 2nd peak as greater in magnitude than the 1st (P21) in the cardiac electrical quantum power spectrum, which clinically speaking means insufficient perfusion to myocardium.

FIG. 6B (43) refers to a simplified graphical depiction of the 2nd peak as greater in magnitude than the 1st (P21) in cardiac electrical of quantum power spectrum, which clinically speaking means insufficient perfusion to myocardium.

Figure 6C:
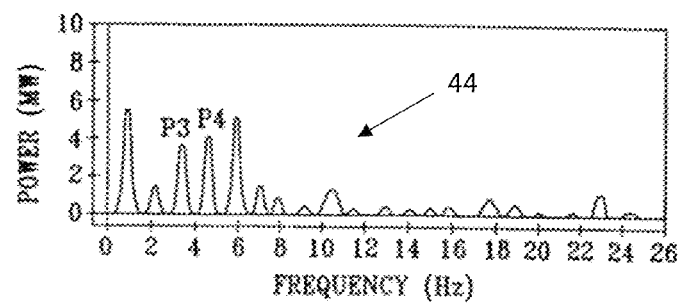
FIG. 6C shows simplified graphical depiction of the 4th peak as greater in magnitude than the 3rd (P43) in the cardiac electrical quantum power spectrum, which clinically speaking means mild insufficient perfusion to myocardium.

FIG. 6C (44) refers to a simplified graphical depiction of the 4th peak as greater in magnitude than the 3rd (P43) in the cardiac electrical quantum power spectrum, which clinically speaking means insufficient perfusion to myocardium.

Figure 6D:
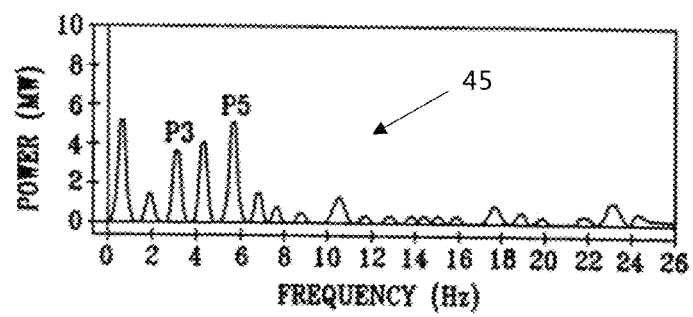
FIG. 6D shows simplified graphical depiction of 5th peak as greater in magnitude than the 3rd (P53) in the cardiac electrical quantum power spectrum, which clinically speaking means mild insufficient perfusion to myocardium.

FIG. 6D (45) refers to a simplified graphical depiction of 5th peak as greater in magnitude than 3rd (P53) in the cardiac electrical quantum power spectrum, which clinically speaking means mild insufficient perfusion to myocardium.

Figure 6E:
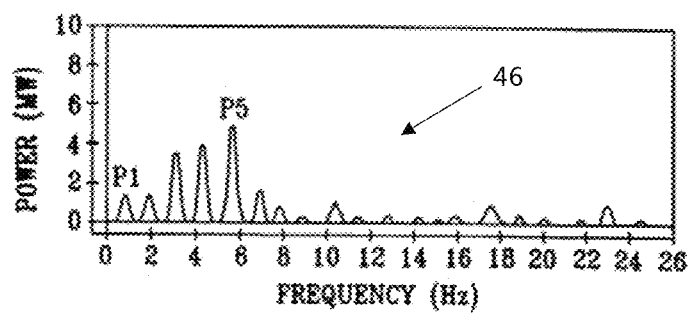
FIG. 6E shows simplified graphical depiction of the 5th peak as greater in magnitude than the 1st (P51) in the cardiac electrical quantum power spectrum, which clinically speaking means insufficient perfusion to myocardium and presence of a compensated hyper dynamic ventricular response.

FIG. 6E (46) refers to a simplified graphical depiction of the 5th peak as greater in magnitude than the 1st (P51) in the cardiac electrical quantum power spectrum, which clinically speaking means insufficient perfusion to myocardium and presence of a compensated hyper-dynamic ventricular response.

Figure 6F:
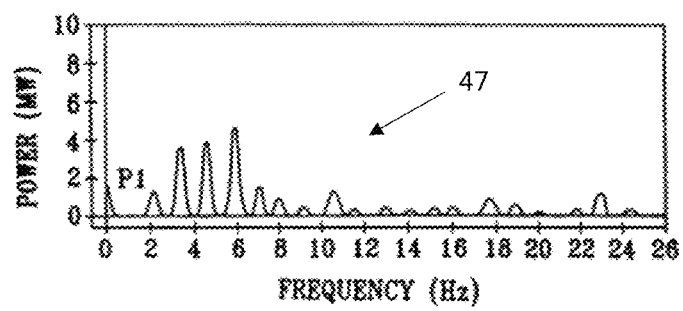
FIG. 6F shows simplified graphical depiction of the 1st peak as relatively low (L01) in magnitude in the cardiac electrical quantum power spectrum, which clinically speaking means previous myocardial injury or scarring.

FIG. 6F (47) refers to a simplified graphical depiction of 1st peak as relatively low (L01) in magnitude in cardiac electrical quantum power spectrum, which clinically speaking means previous myocardial injury or scarring.

Figure 6G:
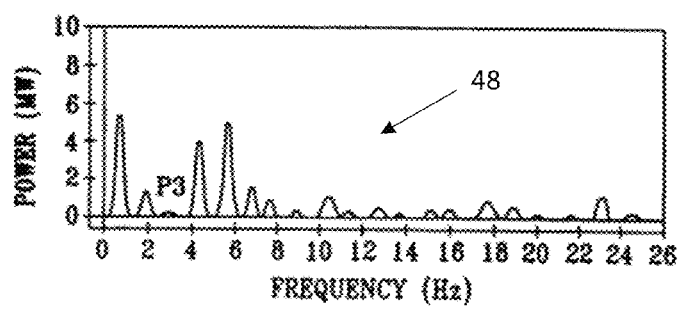
FIG. 6G shows simplified graphical depiction of the 3rd peak as relatively low (L03) in magnitude in the cardiac electrical quantum power spectrum, which clinically speaking means previous myocardial injury or scarring.

FIG. 6G (48), a simplified graphical depiction of 3st peak as relatively low (L03) in magnitude in cardiac electrical quantum power spectrum, which clinically speaking means previous myocardial injury or scarring.

Figure 6H:
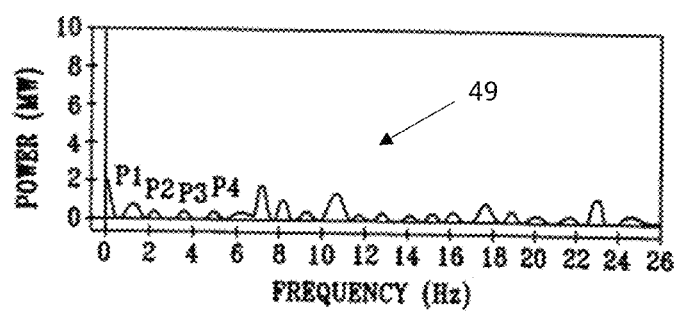
FIG. 6H shows simplified graphical depiction of the average amplitude of the first, second, third, and fourth peaks as relatively low (L0A) in the cardiac electrical quantum power spectrum, which clinically speaking means insufficient perfusion to myocardium and previous myocardial injury or scarring.

FIG. 6H (49) refers to a simplified graphical depiction of Average amplitude of the first, second, third, and fourth peaks as relatively low (LOA) in cardiac electrical quantum power spectrum, which clinical speaking means insufficient perfusion to myocardium and previous myocardial injury or scarring.

Figure 6I:
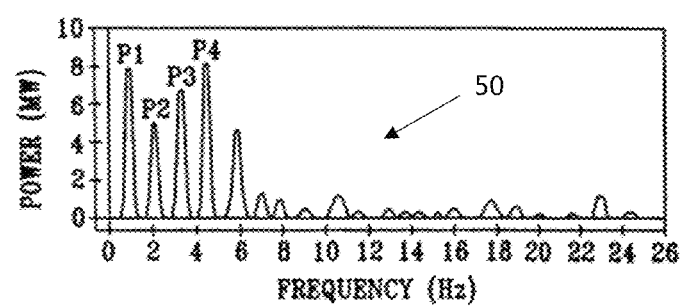
FIG. 6I shows simplified graphical depiction of the average amplitude of the first, second, third, and fourth peaks as relatively high (LVH) in the cardiac electrical quantum power spectrum, which clinically speaking means high voltage and indicates damage of the left ventricle.

FIG. 6I (50) refers to a simplified graphical depiction of Average amplitude of the first, second, third, and fourth peaks as relatively high (LVH) in cardiac electrical quantum power spectrum, which clinically speaking means high voltage in the left ventricle.

FIG. 7A (51) refers to a simplified graphical depiction of a Phase Shift of cardiac electrical signal quantum power spectrum between dual leads. Phase Shift figure on the left is normal and Phase Shift figure on the right is abnormal. The clinical significance of abnormal Phase Shift is poor circulation or hemodynamic changes.

FIG. 7B (52) refers to a simplified graphical depiction of an Impulse Response of cardiac electrical signal quantum power spectrum between dual leads. The Impulse Response figure on the left is normal, and the Impulse Response on the right is abnormal. The clinical significance of abnormal Impulse Response is poor conduction function, left ventricular dysfunction, and arrhythmia.

FIG. 7C (53) refers to a simplified graphical depiction of a Cross Correlation of cardiac electrical signals quantum power spectrum between dual leads. The left is a normal Cross Correlation map, and the right is an abnormal one. The clinical significance of abnormal left ventricular is high voltage or left ventricular hypertrophy.

FIG. 7D (54) refers to a simplified graphical depiction of a Coherence schematic of cardiac electrical signal quantum power spectrum between dual leads. The coherence diagram on the left is normal, and the diagram on the right is abnormal. The clinical significance of the abnormal coherence is sometimes, arrhythmia.

FIG. 8 (55) refers to the base value of f0 as a division of the cardiac electrical schematic diagram of the power spectrum of the quantum, 56 is the base value frequency, 57 is less than the base value of the area integral, and 58 is greater than the base value of the area integral. The value of f0 as a dividing cardiac electrical schematic of the power spectrum of the quantum. This is an important measure of the invention, the base value with a quantum power spectrum is divided into two parts, with a ratio of two parts to determine whether myocardial ischemia is detected. The unit of output is Hz. This new patent indicates that this alone is not enough, it must be used in conjunction with the P21, P51 evaluation criteria for very accurate diagnosis. f0 was measured and calculated in the clinical trials to find the correlations to disease, ischemia, and location of clogging in the RCA, LAD and LCX.

FIG. 9 refers to a simplified graphical depiction of the frontal and lateral surfaces of the lead distribution (59,60) and the location map of the evaluation standard histogram (61,62). The left histogram 61a, 61b, 61c, 61d, 61e, 61f represents the evaluation standard frontal leads, the right histogram 62a, 62b, 62c, 62d, 62e, 62f represents the evaluation standard lateral face of leads, square columns above the dividing line as normal, with green, square column below the dividing line as abnormal, with red.

FIG. 10A (65) refers to the rotating 3D cartography diagnosis of insufficient perfusion to myocardium, myocardial ischemia or myocardial infarction. The 3D map of the heart can rotate to represent the place of insufficient perfusion to myocardium, myocardial ischemia or myocardial infarction. The rotation of the 3D position of the base figure is the ratio of the value of the area integral evaluation standard and the P21, P51 abnormal combination with each other. FIG. 10A (64) refers to a legend of a normal healthy human.

FIG. 10B (65) refers to a legend of myocardial ischemia in patients with coronary artery disease, the shadow representing place of insufficient perfusion to myocardium, myocardial ischemia or myocardial infarction.

FIGS. 11A-11B (66) refers to a simplified graphical depiction of the LOCATIONAL diagnosis of insufficient perfusion to myocardium, myocardial ischemia or myocardial infarction for three major coronary occlusion sites.

FIG. 11A (67) refers to a front view diagram, 68 is the left anterior descending artery (LAD) and its branch vessels, If there is an abnormality in one of the following combinations or groups, it indicates that the left anterior descending artery (LAD) artery and its branches has insufficient perfusion to myocardium, myocardial ischemia or myocardial infarction.

| (1) V1 + V2 + V3 + V4 | --- | Anteroseptal |
| (2) V2 + V3 + V4 + V5 | --- | Anterior |
| (4) I + aVL + V3 + V4 + V5 + V6 | --- | Anterolateral |
| (5) I + aVL + V5 + V6 | --- | idewalls (Lateral) |
| (10) I + III + aVL | --- | aVL lead district |
| (12) V1 + V2 + V6 | --- | V1 lead zone |
| (13) V1 + V2 + V3 | --- | V2 lead zone |
| (14) V2 + V3 + V4 | --- | V3 lead zone |
| (15) V3 + V4 + V5 | --- | V4 lead zone |
| (16) V4 + V5 + V6 | --- | V5 lead area |
| (17) V5 + V6 + V1 | --- | V6 lead zone |
| (18) V1 + V2 | --- | Septal |

69 is a right coronary artery (RCA) and branch vessel. If there is an abnormality in one of the following combination or group, it indicates the right coronary artery (RCA) and it branch vessels indicates insufficient perfusion to myocardium, myocardial ischemia or myocardial infarction.

| (3) II + aVF + V1 + V2 | --- | Inferior Posterior |
| (7) II + aVR + aVF | --- | II lead zone |
| (8) III + aVL + aVF | --- | III lead zone |
| (9) I + II + aVR + V5 | --- | aVR lead zone |
| (11) II + III + aVF | --- | aVF lead zone |
| (19) II + aVF | --- | Inferior |

FIG. 11B (70) is a rear view and 71 is the circumflex artery (LCX) and its branch vessels. Abnormality in one of the following combination or groups indicates that the left circumflex artery (LCX) and its branch vessels has insufficient perfusion to myocardium, myocardial ischemia or myocardial infarction.

(5) I+aVR+aVL+V6--- I lead zone

FIG. 12A-D (71) refers to a simplified graphical depiction of the human heart level, the human heart from the normal, sub-health, unhealthy patient, to critically ill patient, divided into 10 levels.

FIG. 12A (72) is 1-3, Normal, healthy person, in green.
FIG. 12B (73) is 4-6, Sub-Health, sub-health group, in yellow.

FIG. 12C (74) is 7-8, Unhealthy Patient, and has entered the stage of cardiovascular disease, in orange, 7 being less serious and 8 being more serious.

FIG. 12D (75) is 9-10, Critically Ill Patient, myocardial infarction, sudden death or cardiac risks, shown in red.

FIG. 13 shows nine ECG signal amplification circuits. A total of nine road signals to the first right-hand RA signals, for example, a total of three amplifiers 76,87,90. ECG signal received by the right hand resistor 77 (430K Ω), the other end of the resistor 77 and the positive input terminal of the amplifier 76 and a resistor 78 (20K Ω) and a capacitor 79 (0.01μ) connected to the output signal of the amplifier 76 is connected to the capacitor 80 (0.68μ), and then the resistor 81 (33K Ω) and a resistor 82 (2.2 M Ω) is connected. Other end of the resistor 82 is grounded. The other end of the resistor 81 and the resistor 83 (20K Ω) and a capacitor 85 (0.4μ) is connected to the other end of the capacitor 85, which is connected to the output terminal of the amplifier 87, the other end of the resistor 83 and the positive input of amplifier 84 and capacitor 87 (0.01μ) connected to the other end of the capacitor 84 is grounded. Input of amplifier 87 and the negative input terminal connected to the resistor together 86 (1K Ω), and then connected to the positive input terminal of amplifier 90 and a resistor 89 (47K Ω) and a capacitor 88 (0.01μ). The negative input amplifier 87 is grounded. The other end of the resistor 89 and the other end of the capacitor 88 and the output terminal of to the amplifier 90, the output signal is RA-1.

Similarly, the second way to 9-way signal LA, LF, V1, V2, v3, V4, V5, V6 also after three amplified output signal for LA-1, LF-1, V1-1, V2-1, V3-1, V4-1, V5-1, V6-1.

FIG. 14 refers to a diagram of the analog to digital conversion circuity, 92, eight road amplified signal LA-1, LF-1, V1-1, V2-1, V3-1, V4-1, V5-1, V6-1 input to the switch 93 (CD4501) pin 13,14,15,12,1,5,2,4, switch 93 in the three control pins 11,10,9 it turns strobe 8 signal to pin 3, input to the other switch 95 (CD4501) of the pin 13, the signal LF-1 input to the switch 94 (CD4501) of the pin 13, the switch 94 at three selected control pins 11,10,9 through this one-way signal to pin 3, the input to another switch 95 of the pin 14 of the switch 95 under the control of a pin 11, which in turn two strobe signals 13 and 14 to pin 3, the output to the AD conversion chip 98 (AD574) input terminal 13. Chip 97 (GAL20V8) pin 2,3,4,5,6,7,8,9,10,11 host computer expansion slot 99 address lines A0-A9 are connected by pins 17 and the host computer expansion slot 99 data lines D0-D4 together control 96 (74L5373), controlled 98, 96 by pins 19-22, 93 and 94 by pins 2,15,16 control signals through the digital signal gating get 98 points 2 host to the computer expansion slots of 99 data lines D0-D7, 1st high 8 bits, 2nd low 4 bits. Expansion slot on the digital signal can be directly obtained and processed by the computer software.

FIG. 15 refers to each part of the flowchart in the present invention of an application of cardiac electrical signal via the frequency domain, time domain, spatial domain, and the detection and diagnosis of a variety of cardiovascular disorders and level of heart condition; this is a comprehensive analysis using novel methods, systems and instrument.

The following instructions from the principle of the quantum power spectrum of a 12-lead, phase shift, impulse response, cross correlation, coherence. Use of software available on the host computer expansion slot 9-channel digital signal LA, LF, V1, V2, v3, V4, V5, V6, According to the conventional 12-lead standard definition can be deduced conventional 12-lead I=LA−RA
II=LF−RA
III=LF−LA
aVR=RA−(RA+LA+LF)/3
aVL=LA−(RA+LA+LF)/3
aVF=LF−(RA+LA+LF)/3
V1=V1−(RA+LA+LF)/3
V2=V2−(RA+LA+LF)/3
V3=V3−(RA+LA+LF)/3
V4=V4−(RA+LA+LF)/3
V5=V5−(RA+LA+LF)/3
V6=V6−(RA+LA+LF)/3

With the standard 12-lead data, the obtained Fourier transform S [i] (f) and the complex conjugated Fourier transform S [i] (f)*, where i takes 1-12, representative lead number, f (frequency) is S [i] is a function of frequency. Thus, quantum power spectrum P [i] can be obtained by the following formula:

$$P[i]=S[i](f) \cdot S[i](f)^*$$

The phase shift θxy (f) between the double lead for Phase shift $$\theta_{xy}(f) = \tan^{-1}\frac{IMAGX}{REALX},$$
$$X = \frac{G_{xy}(f)}{G_{xx}(f)}$$

Where $|H_{xy}(f)|$ is amplitude ratio of transfer function, $\theta_{xy}$ (f) is the phase shift. $G_{xy}(f)$ is the cross power spectrum of two leads of Cardiac electrical signals, $G_{xx}(f)$ is the auto power spectrum of the lead x. The vertical lines represent modulo.

The Impulse response between the double lead for $$|Hx(f)| = \frac{G_{xy}(f)}{G_{xx}(f)}$$

From the calculating expressions of impulse response, we know the impulse response responds to unit excitation at point x. The response ration excited at points x1 and x2 is represented by expression:

$$X_2(t)=\int_{-\infty}^{\infty} IH_{x1x2}(t)x_1(t-\tau)d\tau$$

The cross-correlation between the double lead for $$\phi_{xy}(\tau) = \lim_{T \to \infty}\frac{1}{2T}\int_{-T}^{T}\hat{f}_x(t) \cdot f_y(t+\tau)dt$$

is applied to the analysis of electrocardio signals, the meaning of each symbol is as follows: $\Phi_{xy}$, τ represents the cross correlation function of electrocardio, t is time, τ is time lag (or is called time delay), $f_y(t)$ and $f_x(t)$ are two leads of Cardiac electrical signal. The subscripts x and y express two different leads of Cardiac electrical signals, 2T (i.e. from −T to T) is the record time of electrocardiogram. In general, we take 2T as 3.

The coherence function between two leads of Cardiac electrical signals of x (t) and y (t) is $$\gamma_{xy}^2(f)=|G_{xy}(f)|/G_{xx}(f)G_{yy}(f)$$

Because the amplitude of cross power spectrum possesses an important relation expression, i.e. inequality of cross spectrum:

$$|G_{xy}(f)|^2 \leq G_{xx}(f)G_{yy}(f)$$

hence $$0 \leq \frac{|G_{xy}(f)|^2}{G_{xx}(f)G_{yy}(f)} \leq 1$$

Therefore the value of coherence function is between 0 and 1.

Quantum power spectrum computing of the present invention is directed to a continuous 12-lead Cardiac electrical signals synchronization conducted Cardiac electrical signals, this period of time comprises a duration in excess of one second, and preferably a duration of generally about 90 seconds.

Additionally, found that in clinical practice that the evaluation criteria using the base value of the area integral of incomplete was missing some important information. The present invention further combines anomaly evaluation criteria using the base value of the area integral with the P21, P51, and in this way obtains more accurate targeting criteria. And using a rotating 3D stereoscopic view of the heart, one can visualize insufficient perfusion to myocardium, myocardial ischemia or myocardial infarction position, which on the 3D model appears red, as shown. Physicians and patients can directly see the specific location of insufficient perfusion to myocardium, myocardial ischemia or myocardial infarction.

Additionally found that the present invention can diagnosis congestive heart failure (CHF), dilated cardiomyopathy (DCM), CAD, MI, ventricular hypertrophy, AF, and other diseases paracytic, a total of 12 kinds of diseases. Coronary heart disease—P21, P51, LOA, MPI, PHS, mutual combinations. For example P21, P51 of II lead and V5 leads all "+", with PHS is "+" can be sentenced for CAD; P21, P51 of II and V5 leads has 3 and 3 above is "+", plus in LOA, MPI, PSH, SWP 4 indicators for 1 a "+" can be sentenced for CAD; P21, P51 has 10 or more for the "+", with MPI, WMP, SWP, USW, PHS 5 indicators there are two for the "+" can be judged as CAD; MI-. P21, P51, LO1, L02, MPI, PHS, SWP, MPL, mutual combinations, ventricular hypertrophy—HAP MPH combination with each other and; for example, two, and two more the "+" in HAP, plus in MPH as "+", can be judged as ventricular hypertrophy; HAP appeared five and five more as "+", can be judged as ventricular hypertrophy; HAP appear two and two more for the "+", with ECG diagnosis ventricular hypertrophy, can be judged as ventricular hypertrophy; MPH as "+", together with the ECG diagnosis of ventricular hypertrophy, can be judged as ventricular hypertrophy; pulmonary heart disease—P21, P51 and MPH (V1, III, aVL lead anomalies) in combination with each other; small vessel disease—PHS and P43, P53 combined with each other; chronic blood disease—P21, P51, P43, P53 and MPL, PHS combined with each other; AF (Fibrillation)—ECG, P wave disappeared, a small f-wave frequency is 350-600 beats/min Cardiac electrical quantum spectrum USW unusual, both in combination with each other; ventricular arrhythmia-. ECG, ventricular premature contraction, ventricular tachycardia, ventricular fibrillation (VF) and ventricular flutter (VEL). Cardiac electrical quantum spectrum PL1, PL2 unusual, both in combination with each other; supraventricular arrhythmias, ECG, supraventricular tachycardia, atrial-ventricular node reentrant tachycardia, atrial-ventricular reentrant tachycardia, atrial-tachycardia. Cardiac electrical quantum spectrum PL1, PL2 unusual, both in combination with each other. Congestive heart failure (CHF)—P21, P51, WMP, USW and arrhythmia in ECG combination with each other, Dilated cardiomyopathy (DCM))—P21, P51, LOA, LO1, LO2, HAP and QRS in ECG combination with each other The invention unites the heart's electrical information, the time domain, the frequency domain, and spatial domain under one unified method, diagnostic system, and instrument. It greatly improves the detection and diagnosis of cardiovascular function and its sensitivity and specificity. (Cardiac electrical information in the time domain of the present invention, the frequency domain, spatial domain fused in a unified method, a diagnostic system, an instrument. Enable the analysis of human cardiac electrical information reaches the holographic level of analysis, greatly improving cardiovascular function Detection and diagnosis of sensitivity and specificity).

It will be understood that various modifications can be made to the various embodiments of the present invention herein disclosed without departing from the spirit and scope thereof. For example, various devices are contemplated as well as various types of construction materials. Also, various modifications may be made in the configuration of the parts and their interaction. Therefore, the above description should not be construed as limiting the invention, but merely as an exemplification of preferred embodiments thereof.

Those of skill in the art will envision other modifications within the scope and spirit of the present invention as defined by the claims appended hereto.

What is claimed is:

1. A method to diagnose heart health by placing a plurality of electrocardiogram (ECG) leads on a patient's body to collect a plurality of electrical signals, analyzing a quantum spectrum to determine a perfusion to a myocardium on a scale of one to five; namely, (1) normal amount of perfusion to said myocardium; (2) mild deficit perfusion to said myocardium; (3) moderate deficit perfusion to said myocardium; (4) severe perfusion deficit to said myocardium; (5) ischemia.

2. The method of claim 1 wherein a combination of an analysis of a frequency domain and a time domain can identify any one selected from a group consisting of the following disease states: coronary heart disease, myocardial infarction, ventricular hypertrophy, pulmonary heart disease, small vessel arrhythmia, supraventricular arrhythmia detection, congestive heart failure, and dilated cardiomyopathy.

3. The method of claim 1 wherein an analysis of a frequency domain can identify any one selected from a group consisting of the following disease states: poor conduction function, poor systemic blood circulation, change of blood dynamics, left ventricular dysfunction, high voltage in the left ventricle, prior injury to the myocardium, and arrhythmia.

\* \* \* \* \*